(12) United States Patent
Boatman et al.

(10) Patent No.: US 7,485,250 B2
(45) Date of Patent: Feb. 3, 2009

(54) MEDICAL DEVICE INCLUDING IMPROVED EXPANDABLE BALLOON

(75) Inventors: Scott E. Boatman, Bloomington, IN (US); David G. Burton, Bloomington, IN (US); Michael C. Hoffa, Bloomington, IN (US); David R. Lessard, Bloomington, IN (US); David A. Drewes, Jr., Bloomington, IN (US); Maggie A. Z. Hupcey, Indianapolis, IN (US)

(73) Assignee: Cook Incorporated, Bloomington, IN (US)

( * ) Notice: Subject to any disclaimer, the term of this patent is extended or adjusted under 35 U.S.C. 154(b) by 672 days.

(21) Appl. No.: 10/463,749

(22) Filed: Jun. 16, 2003

(65) Prior Publication Data
US 2004/0073164 A1    Apr. 15, 2004

Related U.S. Application Data

(62) Division of application No. 09/663,747, filed on Sep. 15, 2000, now Pat. No. 6,592,550.

(60) Provisional application No. 60/154,675, filed on Sep. 17, 1999.

(51) Int. Cl.
*B29C 35/08* (2006.01)
*D01F 1/02* (2006.01)
*A61M 29/00* (2006.01)

(52) U.S. Cl. ............... 264/494; 264/454; 264/456; 264/459; 264/463; 264/523; 264/171.28; 264/211; 264/331.19; 604/103.06

(58) Field of Classification Search ............... None
See application file for complete search history.

(56) References Cited

U.S. PATENT DOCUMENTS 3,864,433 A * 2/1975 Tatsukami et al. ........... 525/197

(Continued)

FOREIGN PATENT DOCUMENTS

EP    0 872 258 A2    10/1998

(Continued)

OTHER PUBLICATIONS

Flesher, Joseph R., "*Polyether block amide: High-Performance TPE*", Modern Plastics, (Sep. 1987), 4 pages beginning @ p. 100.

(Continued)

*Primary Examiner*—Monica A Huson
*Assistant Examiner*—Jeff Wollschlager
(74) *Attorney, Agent, or Firm*—Brinks Hofer Gilson & Lione

(57) ABSTRACT

A medical device (10) includes a catheter shaft (11) including inner and outer catheter shafts (12 and 14), and an expandable balloon (18) carried by the catheter shaft (11). The balloon (18) is made from an irradiation cross-linked mixture of a polyamide elastomer and at least one additional cross-linking reactant. The polyamide elastomer can be a polyester amide, a polyether ester amide or a polyether amide, and is preferably a nylon block copolymer. The cross-linking reactant can be: (a) a difunctional material, (b) a trifunctional material, (c) a tetrafunctional material, or (d) an aromatic molecule containing at least two ring substituents, each of the ring substituents having labile hydrogens at a benzylic site therein. The cross-linking reactant can also be diallyl phthalate or metaphenylene dimaleimide. Irradiation is carried out by exposure to an electron beam or to ultraviolet, X- or gamma radiation, preferably at a total fluence of about 0.5 to about 20 megarads. The amount of the cross-linking reactant is selected to avoid the formation of gelling during the process by which the balloon (18) is made, and the amount of the cross-linking agent and the irradiation fluence are selected to give the balloon a strength generally about equal to that which would be obtained by mere irradiation.

16 Claims, 2 Drawing Sheets

U.S. PATENT DOCUMENTS

| | | | | |
|---|---|---|---|---|
| 4,000,216 A * | 12/1976 | Lang | ............................ | 525/66 |
| 4,154,244 A | 5/1979 | Becker et al. | ............... | 128/349 |
| 4,172,859 A | 10/1979 | Epstein | ........................ | 428/402 |
| 4,191,231 A | 3/1980 | Winchell | ........................ | 150/8 |
| 4,212,965 A | 7/1980 | Campbell | .................... | 528/340 |
| 4,264,658 A * | 4/1981 | Tobias et al. | ................. | 427/518 |
| 4,290,428 A | 9/1981 | Durand et al. | .............. | 128/349 |
| 4,444,816 A | 4/1984 | Richards et al. | ............... | 428/36 |
| 4,490,421 A | 12/1984 | Levy | ............................ | 428/35 |
| 4,617,355 A | 10/1986 | Gabbert et al. | .............. | 525/420 |
| 4,665,557 A | 5/1987 | Kamp | .......................... | 383/63 |
| 4,753,980 A | 6/1988 | Deyrup | ........................ | 524/369 |
| 4,861,830 A | 8/1989 | Ward, Jr. | ..................... | 525/92 |
| 4,906,244 A | 3/1990 | Pinchuk et al. | ............. | 606/194 |
| 4,938,676 A | 7/1990 | Jackowski et al. | .......... | 425/140 |
| 4,950,239 A | 8/1990 | Gahara et al. | ................ | 604/96 |
| 4,963,313 A | 10/1990 | Noddin et al. | .............. | 264/573 |
| 4,964,409 A | 10/1990 | Tremulis | ..................... | 128/657 |
| 5,017,325 A | 5/1991 | Jackowski et al. | .......... | 264/521 |
| 5,036,118 A | 7/1991 | Martinez | ................... | 523/212 |
| 5,049,109 A | 9/1991 | Radovic et al. | .............. | 452/97 |
| 5,051,941 A | 9/1991 | Takamine et al. | ........... | 364/578 |
| 5,055,024 A | 10/1991 | Jackowski et al. | .......... | 425/140 |
| 5,108,415 A | 4/1992 | Pinchuk et al. | ............. | 606/194 |
| 5,156,612 A | 10/1992 | Pinchuk et al. | ............. | 606/194 |
| 5,208,269 A | 5/1993 | Brown | ........................ | 521/125 |
| 5,223,205 A | 6/1993 | Jackowski et al. | .......... | 264/521 |
| 5,236,659 A | 8/1993 | Pinchuk et al. | ............. | 264/573 |
| 5,264,260 A | 11/1993 | Saab | ........................... | 428/35.5 |
| 5,270,086 A | 12/1993 | Hamlin | ....................... | 428/35.2 |
| 5,295,962 A | 3/1994 | Crocker et al. | .............. | 604/101 |
| 5,304,197 A | 4/1994 | Pinchuk et al. | ............. | 606/194 |
| 5,304,340 A | 4/1994 | Downey | ...................... | 264/521 |
| 5,306,246 A | 4/1994 | Sahatjian et al. | .............. | 604/96 |
| 5,318,587 A | 6/1994 | Davey | ......................... | 606/194 |
| 5,324,564 A * | 6/1994 | Chiotis et al. | ................ | 428/124 |
| 5,328,468 A | 7/1994 | Kaneko et al. | ................ | 604/96 |
| 5,330,428 A | 7/1994 | Wang | ........................... | 604/96 |
| 5,338,296 A | 8/1994 | Dalessandro et al. | .......... | 604/96 |
| 5,342,386 A | 8/1994 | Trotta | ......................... | 606/194 |
| 5,344,401 A | 9/1994 | Radisch et al. | ............... | 604/96 |
| 5,356,591 A | 10/1994 | Pinchuk et al. | ............. | 264/573 |
| 5,382,633 A * | 1/1995 | Scott et al. | ................... | 525/279 |
| 5,385,173 A | 1/1995 | Gargiulo | ..................... | 138/98 |
| 5,423,838 A | 6/1995 | Willard | ....................... | 606/159 |
| 5,433,713 A | 7/1995 | Trotta | ......................... | 604/264 |
| 5,449,371 A | 9/1995 | Pinchuk et al. | ............. | 606/194 |
| 5,451,747 A | 9/1995 | Sullivan et al. | ............. | 219/528 |
| 5,522,961 A | 6/1996 | Leonhardt | ................... | 156/252 |
| 5,531,715 A | 7/1996 | Engelson et al. | ............ | 604/265 |
| 5,545,133 A | 8/1996 | Burns et al. | .................... | 604/96 |
| 5,554,120 A | 9/1996 | Chen et al. | .................... | 604/96 |
| 5,556,383 A | 9/1996 | Wang et al. | ................... | 604/96 |
| 5,565,523 A | 10/1996 | Chen et al. | .................... | 525/176 |
| 5,620,649 A | 4/1997 | Trotta | ......................... | 264/515 |
| 5,670,097 A * | 9/1997 | Duan et al. | ................. | 264/1.24 |
| RE35,717 E | 1/1998 | Nahm | ......................... | 526/166 |
| 5,714,110 A | 2/1998 | Wang et al. | .................. | 264/529 |
| 5,728,063 A | 3/1998 | Preissman et al. | ............. | 604/96 |
| 5,731,365 A * | 3/1998 | Engelhardt et al. | .......... | 523/206 |
| 5,738,653 A | 4/1998 | Pinchuk et al. | ................ | 604/96 |
| 5,747,591 A | 5/1998 | Chen et al. | .................... | 525/176 |
| 5,755,690 A | 5/1998 | Saab | ........................... | 604/96 |
| 5,769,817 A | 6/1998 | Burgmeier | ..................... | 604/96 |
| 5,795,325 A | 8/1998 | Valley et al. | .................. | 604/53 |
| 5,797,877 A | 8/1998 | Hamilton | ..................... | 604/96 |
| 5,807,520 A | 9/1998 | Wang et al. | .................. | 264/520 |
| 5,826,588 A | 10/1998 | Forman | ...................... | 128/898 |
| 5,830,182 A | 11/1998 | Wang et al. | ................... | 604/96 |
| 5,833,657 A | 11/1998 | Reinhardt et al. | ............. | 604/96 |
| 5,836,951 A * | 11/1998 | Rosenbluth et al. | ......... | 606/108 |
| 5,900,444 A | 5/1999 | Zamore | ....................... | 522/137 |
| 5,919,570 A | 7/1999 | Hostettler et al. | ......... | 428/424.8 |
| 5,951,494 A | 9/1999 | Wang et al. | .................. | 600/585 |
| 5,951,941 A | 9/1999 | Wang et al. | ................... | 264/523 |
| 5,977,254 A * | 11/1999 | Mc Kee et al. | ................. | 525/64 |
| 5,998,551 A * | 12/1999 | O'Neil et al. | ................ | 525/426 |
| RE36,717 E | 5/2000 | Thompson | .................. | 426/518 |
| 6,093,463 A * | 7/2000 | Thakrar | ...................... | 428/36.9 |
| 6,139,998 A * | 10/2000 | Mochizuki et al. | ............ | 430/56 |
| 6,261,260 B1 * | 7/2001 | Maki et al. | ............... | 604/103.07 |
| 6,492,443 B1 * | 12/2002 | Kodemura et al. | ............ | 524/114 |
| 6,524,673 B1 * | 2/2003 | Bhattacharyya | ............ | 428/36.9 |
| 6,596,818 B1 * | 7/2003 | Zamore | ........................ | 525/426 |
| 6,656,550 B1 * | 12/2003 | Zamore | ....................... | 428/35.7 |

FOREIGN PATENT DOCUMENTS

| | | |
|---|---|---|
| WO | WO 96/17883 | 6/1996 |
| WO | WO 98/15199 | 4/1998 |
| WO | WO 98/55171 | 12/1998 |
| WO | WO 99/29353 | 6/1999 |
| WO | PCT/US 00/25258 | 9/2000 |

OTHER PUBLICATIONS

Acquarulo, Lawrence A., et al., "Cross-Linking Thermoplastic Elastomers for Improved Product Performance", Medical Plastics and Biomaterials Special Section, Medical Device & Diagnostic Industry, (Jun. 1999), 6 pages beginning @ p. 116.

Technical Information; Pebax Resins, 33 Series Property Comparison, 1 page, date unknown.

* cited by examiner

MEDICAL DEVICE INCLUDING IMPROVED EXPANDABLE BALLOON

CROSS-REFERENCE TO RELATED APPLICATIONS

This application is a division of application Ser. No. 09/663,747, filed Sep. 15, 2000, now U.S. Pat. No. 6,592,550, which claims priority to provisional application Ser. No. 60/154,675, filed Sep. 17, 1999, which is hereby incorporated by reference.

TECHNICAL FIELD

This invention relates generally to medical devices and, more particularly, to devices for deploying another medical device such as a stent into a patient or for expanding a narrowed or obstructed passage or lumen in a patient.

BACKGROUND OF THE INVENTION

Medical devices which incorporate inflatable or expandable balloons serve a wide variety of purposes. The balloon is carried on or affixed to a catheter shaft for delivery of the balloon to a desired location in the patient. The catheter shaft includes a lumen for introducing an inflation fluid into the balloon. For example, such catheter balloons are widely known to be useful for performing angioplasty procedures or the like, in which narrowings or obstructions in blood vessels or other body passageways are altered in order to increase blood flow through the narrow or obstructed area. More specifically, in a typical balloon angioplasty procedure, a balloon catheter is percutaneously introduced into the patient by way of the arterial system and advanced until the balloon of the catheter lies across the vascular narrowing or obstruction. The balloon is then inflated to dilate the vessel lumen at the site of the narrowing or obstruction. If desired, a stent may be positioned over the balloon and deployed at the site of the narrowing or obstruction to ensure that the dilated vessel lumen remains open. Balloon catheters find utility in a wide range of procedures, including valvuloplasty and urological procedures, among others.

The balloons of prior balloon catheters have been constructed from a wide variety of polymeric materials. These balloons each have their own advantages and drawbacks. Balloons comprising polyethylene terephthalate (PET), for example, have a relatively low degree of distention or expansion once they are inflated. This generally minimizes any potential adverse effects from overinflation or overexpansion of the balloon or any stent carried on it. Semi-distending or non-distending balloons often possess relatively high tensile strength, burst pressure and puncture resistance, qualities highly desirable for dilating tough lesions or for deploying and expanding stents carried over them.

However, body vessels such as arteries are generally tapered, and the locations at which narrowings or obstructions may occur vary, so that a balloon which closely matches the ultimately desired diameter of the vessel may not be readily available. Moreover, it may at times be desirable to be able to increase the diameter of the balloon beyond that which had been contemplated before the balloon procedure was begun. While balloons comprising materials such as polyvinyl chloride can be more distensible than PET or the like, balloons comprising such materials often possess a significantly lower tensile strength, burst pressure or puncture resistance than the less-distensible balloons. Overinflation of such balloons is also possible.

A variety of attempts have been made to construct medical device balloons from materials which yield balloons of good strength (that is, relatively high tensile strength and burst pressure, and good puncture resistance) while retaining an adequate degree of compliance, that is, an acceptable ratio of balloon diameter growth under an applied pressure to that balloon pressure. Each of these attempts possesses its own advantages and disadvantages. Balloons made from materials such as PET may possess excessive crystallinity or may be too stiff, so that such balloons may be resistant to the folding desired to minimize the profile of the catheter in which the balloon is employed; such resistance to folding is particularly problematic when the balloon is deflated following inflation during an in situ application, in order to be retracted into the distal end of the catheter for withdrawal. A minimal catheter profile is a highly desirable characteristic of balloon catheters, however. Some materials do not readily accept coating with drugs or lubricants, and some materials are difficult to fuse or adhere to conventional catheter shafts. Balloons made of some biaxially oriented nylons or polyamides have been asserted to overcome some of these problems.

Catheter balloons comprised of block copolymers have been suggested as a way of achieving an acceptable combination of balloon strength and elasticity. For example, it is known that catheter balloons can be constructed from polyamide/polyether block copolymers, commonly identified by the acronym PEBA (polyether block amide). Many of such copolymers can be characterized by a two phase structure, one being a thermoplastic region that is primarily a polyamide, semicrystalline at room temperature, and the other being an elastomer region that is rich in polyether. Balloons comprising such copolymers are asserted to possess a desirable combination of strength, compliance and softness. Catheter balloons comprising blends of two or more such copolymers are also known, and it has been asserted that irradiating such blends can enhance the properties of the resulting balloons, including increased burst pressures.

It would be highly advantageous to have medical devices which included expandable or inflatable balloons with improved strength, for example, with greater tensile strength, burst pressure and/or puncture resistance, while simultaneously possessing acceptable compliance (in this case, an acceptable ratio of balloon diameter growth to balloon pressure). It would also be highly advantageous to have medical devices made from materials which meet a variety of desirable processing criteria, including thermal stability, non-toxicity, non-volatility, high boiling point (preferably, solid at room temperature), high flash point, insensitivity to moisture and commercial availability.

SUMMARY OF THE INVENTION

Many of the foregoing problems are solved and a technical advance is achieved in an illustrative medical device for positioning an included balloon within a human or veterinary patient, for example, for deploying another medical device such as a stent in the patient or for expanding a passage or lumen in the patient. More particularly, in a first preferred embodiment, the medical device of the present invention comprises a catheter shaft and an expandable balloon carried by the catheter shaft. The medical device of the present invention is characterized in that the balloon comprises an irradiation cross-linked mixture of a polyamide elastomer and at least one additional cross-linking reactant.

This additional cross-linking reactant performs a role which is quite different from that performed by the two reaction promoters disclosed in International Application WO 98/55171. That Application is directed to a cross-linked nylon block copolymer which comprises an irradiation crosslinked copolymer containing a polyamide block and an elastomeric block, including a compound which promotes cross-linking therein. The process disclosed in that application comprises supplying the nylon block copolymer with a cross-linking "promotor" (sic.) and exposing the block copolymer to irradiation sufficient to cross-link the copolymer. Only two promoters are disclosed, triallylcyanurate and triallylisocyanurate, at 2 percent by weight in PEBAX® brand nylon block copolymer (Atochem, Inc., brand of polymers consisting of polyether blocks separated by polyamide blocks). Irradiation is carried out at 5 to 20 megarads (no specific type of irradiation is disclosed), although degradation of the material may take place when total irradiation becomes too high, for example, at 15 or 20 megarads. That Application claims (among others) an improvement in a balloon type catheter having a tubular shaft comprising a nylon block copolymer and an integrally formed balloon section, the improvement comprising irradiation crosslinking the copolymer of the balloon section, wherein the crosslinking lowers the percent elongation of the balloon section as compared to the elongation prior to crosslinking. The only apparent support in the specification for that claim appears to be a single statement that, in the case of balloon catheters manufactured from a nylon block copolymer, the invention therein provides for the preparation of a balloon type catheter wherein the balloon section relative to the shaft can be converted into a thermoset or crosslinked type structure, thereby increasing its overall mechanical strength, performance, and durability. That Application appears to make no other disclosure of any process whatsoever for manufacturing such a balloon, and appears to contain absolutely no details as to how such a process could or should be carried out.

The present invention is quite distinct; the cross-linking reactant of the present invention and the promoter of that Application appear to act in different ways to perform different functions. "Promoter" is a well-recognized term of art, of course, referring to a material which enhances the activity of a catalyst. More particularly, a promoter is a substance that, when added in relatively small quantities to a catalyst, increases its activity; Lewis, Sr., *Hawley's Condensed Chemical Dictionary* 12$^{th}$ (Van Nostrand Reinhold Company, New York, N.Y., 1993) (definition 1), at 966; or is a chemical which itself is a feeble catalyst, but greatly increases the activity of a given catalyst; Parker, *McGraw-Hill Dictionary of Scientific and Technical Terms* 5$^{th}$ (McGraw-Hill, Inc., New York, N.Y., 1994) (first definition), at 1589. Catalysts, of course, accelerate or retard the velocity of a chemical reaction without being consumed during the course of those reactions. They do not become incorporated into the chemical structures of the products of the reactions, and in theory can be recovered at the end of the reaction essentially unaltered in form and amount (even though in practice they might be retained in the physical object constituted by the reaction products). This is presumably true of the two materials mentioned in that Application, since they appear to be solely described in that Application as "promoters." While it might be argued whether energy should properly be called a catalyst, it is believed that the use of the word "promoters" in that Application would be readily understood by those in the medical device field to refer to materials which increased the activity of the irradiation employed in that Application, that is, increased irradiation cross-linking between the chains themselves of the nylon block copolymer it discloses.

In direct contrast to any balloon or medical device containing the two specific promoters of that Application at their disclosed concentrations, the medical device of the present invention comprises a balloon in which one or more specific cross-linking reactants are, by irradiation, chemically incorporated into the polyamide elastomer with which they are initially mixed. Thus, where the two promoters of that Application would cause the various chains within the polyamide elastomer of any balloon to cross-link directly to one another, the specific cross-linking reactants in the balloon of the present invention instead themselves form and constitute links or bridges between the various chains within the polyamide elastomer. Thus, the molecular structure and physical properties of the balloon incorporated in the medical device of the present invention are different from those which might be expected to be possessed by a balloon which included either of the two catalysts or promoters of that Application.

The particular cross-linking reactants useful in the medical device of the present invention, and in particular, in the balloon thereof, are expected to include difunctional materials such as diallyl adipate; diallyl carbonate; diallyl maleate; diallyl succinate; diallyl tetrabromophthalate; diethyl diallylmalonate; dimethyl diallylmalonate; and 2,2,6,6-tetrabromobisphenol A diallyl ether. Useful cross-linking reactants are also expected to include trifunctional materials such as 2,5-diallyl-4,5-dimethyl-2-cyclopenten-1-one; diallyl fumarate; diallyl itaconate; 1,3,5-triallyl-2-methoxybenzene; triallyl trimesate (triallyl 1,3,5-benzenetricarboxylate); triallyl trimellitate (triallyl 1,2,4-benzenetricarboxylate); and pentaerythritol triallyl ether; and tetrafunctional materials such as tetraallyl cis,cis,cis,cis-cyclopentane-1,2,3,4-tetracarboxylate; and N,N,N',N'-tetraallylethylenediamine. Useful materials are also expected to include aromatic molecules containing at least two ring substituents, each of the ring substituents having labile hydrogens at a benzylic site therein. 1,3,5 triethyl benzene; 1,2,4 triethyl benzene; and 1,3,5 triisopropyl benzene are commercially available examples of such aromatic molecules containing at least two substituents having labile hydrogens at a benzylic site. Useful materials are further expected to include diallyl phthalate and meta-phenylene dimaleimide; these latter two constitute a second preferred embodiment of the present invention.

All of these materials are expected to possess at least several of a variety of desirable characteristics for manufacturing the medical device of the present invention: thermal stability, non-toxicity, non-volatility, high boiling point (preferably, solid at room temperature), high flash point, insensitivity to moisture and commercial availability. However, not all of these materials possess all of these desirable characteristics. Other materials capable of forming allylic or benzylic radicals having comparable reactivity should be useful as well. The primary criteria for selecting such other materials may be that they are less reactive than species such as epoxies, methacrylates and acrylates; and that they are relatively "small" molecules, that is, they are small enough to fit between (and thereby be capable of cross-linking) the various chains of the particular polyamide elastomer being used. The materials must of course be multifunctional, to be able to cross-link to at least two of those chains.

The more reactive species such as epoxies, methacrylates and acrylates are probably undesirable for use in the medical device of the present invention because they are likely to cross-link the polyamide elastomer too rapidly, completing the cross-linking reaction during preliminary thermal processing of the polyamide elastomer (prior to its being formed into the balloon of the device). Such premature cross-linking clogs the processing equipment, such that completion of the balloon-forming process is impossible. Multifunctional allylic materials are more stable and less reactive than these, so that they readily survive thermal processing but are still reactive enough when exposed to a source of energy to achieve good cross-linking.

The allylic radical and the benzylic radical differ in bond dissociation energies (and hence radical stabilities and reactivities) by only 2 kcal/mol (7 kJ/mol); J. March, *Advanced Organic Chemistry* $4^{th}$, at 191 (John Wiley & Sons, New York, N.Y., 1992). Accordingly, a wide variety of multifunctional benzylic small molecules are expected to be useful in the medical device of the present invention; the three listed above have the advantage of being commercially available at the present time. The selection of other materials having suitably positioned labile hydrogens should be well within the level of skill in the field of designing medical devices of this type, since the recognition of labile hydrogen positions is generally taught quite early in introductory (college sophomore) organic chemistry.

While some modest degree of trial-by-error experimentation may be needed to confirm the practical utility of any particular allylic or benzylic material contemplated for use in the present invention but not specifically disclosed herein, such experimentation is not believed to be undue under the circumstances, but is instead believed to be substantially below the amount of testing that would be required for FDA approval for actually marketing a medical device incorporating a balloon comprising such a particular material as a cross-linking reactant.

While attempting to manufacture a medical device balloon employing the two promoters disclosed in International Application WO 98/55171, it was discovered that these two specific materials could in fact act as cross-linking reactants (instead of merely augmenting the cross-linking activity of the disclosed irradiation) under concentrations or conditions other than the concentrations or conditions disclosed in that Application. More particularly, attempts to make a parison for forming a medical device balloon from a mixture of PEBAX® brand nylon block copolymer with 2 percent by weight of one of those materials were generally unsuccessful or unacceptable for commercial purposes, due to the significant formation of gelling in the parison. "Gelling" is a term of art which indicates the formation of small, discrete volumes, areas, particles or particulates which are a result of premature, undesirable thermal cross-linking of the copolymer or other polyamide elastomer itself. "Gelling" also includes other defects arising during the manufacture of the copolymer or other polyamide elastomer. Gelling in the particular mixture under consideration prevented the successful use of the resulting parison to form a balloon for commercial purposes.

Since that Application teaches that higher levels of irradiation are undesirable, it is believed that those skilled in the field would have concluded that the only alternative left for improving the amount of cross-linking would have been to increase the amount of promoter mixed with the copolymer. Efforts in this direction were unsuccessful. Unexpectedly, it was found that an acceptable balloon could be obtained by lowering, not increasing, the amount of the promoter. As a result, gelling was decreased to an acceptable level. It was found that at these lower levels the so-called "promoter" itself acted as a cross-linking reactant, incorporated in the structure of the cross-linked copolymer between the chains of the copolymer. Such a result appears to be directly contrary to any reasonable expectation from the disclosure of that Application.

Accordingly, in a third preferred embodiment, the medical device of the present invention comprises a combination which is comparable to the first preferred embodiment, but which is instead characterized in that its balloon is formed from an irradiated mixture of a polyamide elastomer and no more than about 1.5 percent by weight of either triallyl cyanurate or triallyl isocyanurate. It is believed that these two materials advantageously possess most or all of the desirable characteristics mentioned above.

In all of these embodiments of the present invention, the polyamide elastomer can be one or more members of any of the three generally recognized families of polyamide elastomers: polyester amides (or PESAs), polyether ester amides (PEEAs) or polyether amides (PETAs). Representative PESAs include ESTAMID® brand polymer from Dow Chemical Company. Representative PEEAs include PEBAX® brand nylon block copolymer, VESTAMID® brand polymer from Creanova Corporation and GRILAMID® brand polymer from Esmer Corporation. Representative PETAs include GRILON® brand polymer, also from Esmer Corporation.

Other preferred embodiments of the present invention described in more detail below include the processes by which these three embodiments of the medical device of the present invention are assembled. The medical device of the present invention may be particularly advantageous in that the puncture resistance, strength and burst pressure of its balloon may be improved with respect to comparable irradiation cross-linked balloons lacking any cross-linking reactant.

In a first aspect, then, the present invention is directed to a medical device comprising: a catheter shaft; and an expandable balloon carried by the catheter shaft; wherein the balloon comprises an irradiation cross-linked mixture of a polyamide elastomer and at least one additional cross-linking reactant, the cross-linking reactant comprising: (a) a difunctional material selected from the class consisting of diallyl adipate; diallyl carbonate; diallyl maleate; diallyl succinate; diallyl tetrabromophthalate; diethyl diallylmalonate; dimethyl diallylmalonate; and 2,2,6,6-tetrabromobisphenol A diallyl ether; (b) a trifunctional material selected from the class consisting of 2,5-diallyl-4,5-dimethyl-2-cyclopenten-1-one; diallyl fumarate; diallyl itaconate; 1,3,5-triallyl-2-methoxybenzene; triallyl trimesate (triallyl 1,3,5-benzenetricarboxylate); triallyl trimellitate (triallyl 1,2,4-benzenetricarboxylate); and pentaerythritol triallyl ether; (c) a tetrafunctional material selected from the class consisting of tetraallyl cis, cis,cis,cis-cyclopentane-1,2,3,4-tetracarboxylate; and N,N,N',N'-tetraallylethylenediamine; or (d) an aromatic molecule containing at least two ring substituents, each of the ring substituents having labile hydrogens at a benzylic site therein. In a second aspect, the present invention is directed to such a device in which the at least one additional cross-linking agent comprises diallyl phthalate or meta-phenylene dimaleimide.

The balloon of the medical device preferably comprises an amount of the cross-linking reactant sufficient to give the balloon a strength generally about equal to and perhaps in some cases greater than that of a balloon composed of the polyamide elastomer and comparably cross-linked by irradiation, but in the absence of any cross-linking reactant, agent or promoter. The balloon more preferably comprises about 1 to about 2 percent by weight of the difunctional material; about 0.5 to about 1.5 percent by weight of the trifunctional material or the aromatic molecule containing at least two ring substituents, each of the ring substituents having labile hydrogens at a benzylic site therein; or about 0.01 to about 1 percent by weight of the tetrafunctional material. The balloon alternatively comprises about 1 to about 2 percent by weight diallyl phthalate or metaphenylene dimaleimide.

The balloon of the medical device further preferably comprises a mixture of the polyamide elastomer and the cross-linking reactant which has been cross-linked by irradiation with an electron beam or with ultraviolet, X- or gamma rays.

More preferably, the balloon comprises a mixture of the polyamide elastomer and the cross-linking reactant which has been cross-linked by exposure to about 0.5 to about 20 megarads of radiation. It is preferred that the balloon is formed by inflation of the mixture of the polyamide elastomer and the cross-linking reactant after the mixture has been cross-linked by irradiation.

As indicated above, the balloon of the medical device can comprise any member of the polyamide elastomer families, such as polyester amides, polyether ester amides or polyether amides. The balloon preferably comprises a nylon block copolymer including polyamide blocks separated by elastomeric polyether blocks or segments. Suitable nylon block copolymers of this type are sold under the trademark PEBAX® by Atochem, Inc. Useful nylon block copolymers can instead include polyamide blocks separated by other elastomeric blocks or segments, such as polyesters, hydrocarbons or polysiloxanes.

When the balloon comprises an irradiation cross-linked mixture of a polyamide elastomer and an aromatic molecule, it is preferred that the aromatic molecule containing at least two ring substituents, each of the ring substituents having labile hydrogens at a benzylic site therein, is selected from the class consisting of 1,3,5 triethyl benzene; 1,2,4 triethyl benzene; and 1,3,5 triisopropyl benzene.

In a third aspect, the present invention is directed to a medical device comprising: a catheter shaft; and an expandable balloon carried by the catheter shaft; wherein the balloon comprises an irradiation cross-linked mixture of a polyamide elastomer and no more than about 1.5 percent by weight of at least one additional cross-linking reactant, the cross-linking reactant comprising triallyl cyanurate or triallyl isocyanurate. Preferably, the balloon comprises an amount of the cross-linking reactant sufficient to give the balloon a strength generally about equal to and in some cases perhaps greater than that of a balloon composed of the polyamide elastomer and comparably cross-linked by irradiation, but in the absence of any cross-linking reactant, agent or promoter.

In this third aspect, the balloon of the medical device preferably comprises a mixture of the polyamide elastomer and the cross-linking reactant which has been cross-linked by irradiation by an electron beam or by ultraviolet, or X- or gamma rays. Even more preferably, the balloon comprises a mixture of the polyamide elastomer and the cross-linking reactant which has been cross-linked by exposure to about 0.5 to about 20 megarads of radiation. The balloon is preferably formed by inflation of the mixture of the polyamide elastomer and the cross-linking reactant after the mixture has been cross-linked by irradiation.

As in the first aspect of the present invention, the balloon of the medical device of the second and third aspects of the present invention preferably comprises a polyester amide, a polyether ester amide or a polyether amide, and more preferably comprises a nylon block copolymer including polyether blocks separated by polyamide blocks, such as PEBAX® brand nylon block copolymer.

In a fourth aspect, the present invention is directed to a process for assembling a medical device, the medical device comprising an expandable balloon, and the process comprising: creating a mixture of a polyamide elastomer and at least one additional cross-linking reactant, the cross-linking reactant comprising: (a) a difunctional material selected from the class consisting of diallyl adipate; diallyl carbonate; diallyl maleate; diallyl succinate; diallyl tetrabromophthalate; diethyl diallylmalonate; dimethyl diallylmalonate; and 2,2,6, 6-tetrabromobisphenol A diallyl ether; (b) a tri-functional material selected from the class consisting of 2,5-diallyl-4,5-dimethyl-2-cyclopenten-1-one; diallyl fumarate; diallyl itaconate; 1,3,5-triallyl-2-methoxybenzene; triallyl trimesate (triallyl 1,3,5-benzenetricarboxylate); triallyl trimellitate (triallyl 1,2,4-benzenetricarboxylate); and pentaerythritol triallyl ether; (c) a tetrafunctional material selected from the class consisting of tetraallyl cis,cis,cis,cis-cyclopentane-1,2,3,4-tetracarboxylate; and N,N,N',N'-tetraallylethylenediamine; or (d) an aromatic molecule containing at least two ring substituents, each of the ring substituents having labile hydrogens at a benzylic site therein; cross-linking the mixture of the polyamide elastomer and the at least one additional reactant by exposing the mixture to a suitable fluence of radiation; and forming the cross-linked mixture into the balloon. In a fifth aspect of the present invention, this process is instead carried out with at least one additional cross-linking reactant comprising diallyl phthalate or meta-phenylene dimaleimide.

The process of the present invention for assembling the medical device is preferably carried out with an amount of the cross-linking reactant sufficient to give the balloon a strength generally about equal to, and perhaps in some cases greater than, that of a balloon composed of the polyamide elastomer and comparably cross-linked by irradiation, but in the absence of any cross-linking reactant, agent or promoter. It is also preferred that the process is carried out with an amount of the cross-linking reactant which, when mixed with the polyamide elastomer and processed, causes the mixture from which the balloon is made to lack appreciable gelling during processing prior to irradiation and cross-linking. More preferably, the process is carried out with a mixture comprising about 1 to about 2 percent by weight of the difunctional material; about 0.5 to about 1.5 percent by weight of the trifunctional material or the aromatic molecule containing at least two ring substituents, each of the ring substituents having labile hydrogens at a benzylic site therein; or about 0.01 to about 1 percent by weight of the tetrafunctional material. Alternatively, the process can be carried out with about 1 to about 2 percent by weight diallyl phthalate or meta-phenylene dimaleimide.

Cross-linking of the mixture of the polyamide elastomer and the at least one additional reactant preferably comprises irradiating the mixture with an electron beam or with ultraviolet, X- or gamma rays. Irradiation is more preferably carried out at a total fluence of about 0.5 to about 20 megarads.

The process of the present invention is preferably carried out with the polyamide elastomers described above. More preferably, the process of the present invention is carried out with a nylon block copolymer which includes polyether blocks separated by polyamide blocks, such as PEBAX® brand nylon block copolymer. When the process is carried out with an aromatic molecule containing at least two ring substituents, each of the ring substituents having labile hydrogens at a benzylic site therein, it is preferred that the molecule is selected from the class consisting of 1,3,5 triethyl benzene; 1,2,4 triethyl benzene; and 1,3,5 triisopropyl benzene. Without regard to the specific polyamide elastomer and the at least one additional reactant employed in the present invention, however, it is preferred that the mixing of them is carried out by compounding (including such steps as melting, mixing and extruding, for example) or by blending.

The process of the present invention for making a medical device preferably further comprises forming the mixture of the polyamide elastomer and the at least one additional reactant into tubing, from which the balloon is formed. It is further preferred that the tubing is formed by extruding the mixture of the polyamide elastomer and the at least one additional reactant. Most preferably, the mixture of the polyamide elastomer and the at least one additional reactant is then formed into the balloon by inflation of the tubing. The process of the present invention can further comprise connecting the balloon so formed to a catheter shaft, for example, by adhesion or thermal bonding.

In a sixth aspect, the present invention is directed to a process for assembling a medical device, the medical device comprising an expandable balloon, and the process comprising: creating a mixture of a nylon block copolymer and no more than about 1.5 percent by weight of at least one additional cross-linking reactant, the cross-linking reactant comprising triallyl cyanurate or triallyl isocyanurate; cross-linking the mixture of the polyamide elastomer and the at least one additional reactant by exposing the mixture to a suitable fluence of radiation; and forming the cross-linked mixture into the balloon.

Other than the use of these two specific cross-linking reactants at the specified amounts, the preferred details of carrying out the process of this sixth aspect of the present invention are very comparable to the details of carrying out the process of the fourth aspect of the invention. Most notably, cross-linking of the mixture of the polyamide elastomer and the at least one additional reactant preferably comprises irradiating the mixture with an electron beam or with ultraviolet, X- or gamma rays. Irradiation is more preferably carried out at a total fluence of about 0.5 to about 20 megarads. The balloon is preferably formed by inflation of a tubing extruded from the mixture of the polyamide elastomer and the at least one cross-linking reactant, the tubing being irradiated before the balloon is formed from it. The process of the sixth aspect of the present invention is most preferably carried out with a nylon block copolymer including polyether blocks separated by polyamide blocks, such as PEBAX® brand nylon block copolymer.

In a seventh and final aspect, the present invention is directed to a medical device comprising: a catheter shaft; and an expandable balloon carried by the catheter shaft; wherein the balloon comprises an irradiation cross-linked mixture of a polyamide elastomer and at least one additional cross-linking reactant. This aspect of the invention may instead be considered as an improvement in a medical device comprising a catheter shaft and an expandable balloon carried by the catheter shaft, characterized in that the balloon comprises an irradiation cross-linked mixture of a polyamide elastomer and at least one additional cross-linking reactant.

As indicated above, the medical device of the present invention possesses significant advantages over prior devices for dilating a narrowing or obstruction in a vessel or lumen in a patient, and for deploying a stent across the site of such a narrowing or obstruction to prevent its restenosis. The balloon of the device of the present invention has generally improved strength, for example, greater tensile strength, burst pressure and/or puncture resistance, while simultaneously possessing acceptable compliance, that is, an acceptable ratio of balloon diameter growth to balloon pressure. Gelling during its manufacture, if present, is limited to an acceptable level. The balloon of the device of the present invention is made from materials which meet a variety of desirable processing criteria, including thermal stability, non-toxicity, non-volatility, high boiling point (preferably, solid at room temperature), high flash point, insensitivity to moisture and commercial availability. A second polyamide elastomer or another polyamide (such as nylon) may be added in a minor amount (less than 50 percent by weight or mole fraction), but is not required.

BRIEF DESCRIPTION OF THE DRAWINGS

A better understanding of the present invention will now be had upon reference to the following detailed description, when read in conjunction with the accompanying drawing, wherein like reference characters refer to like parts throughout the several views, and in which.

DETAILED DESCRIPTION

Figure 1:
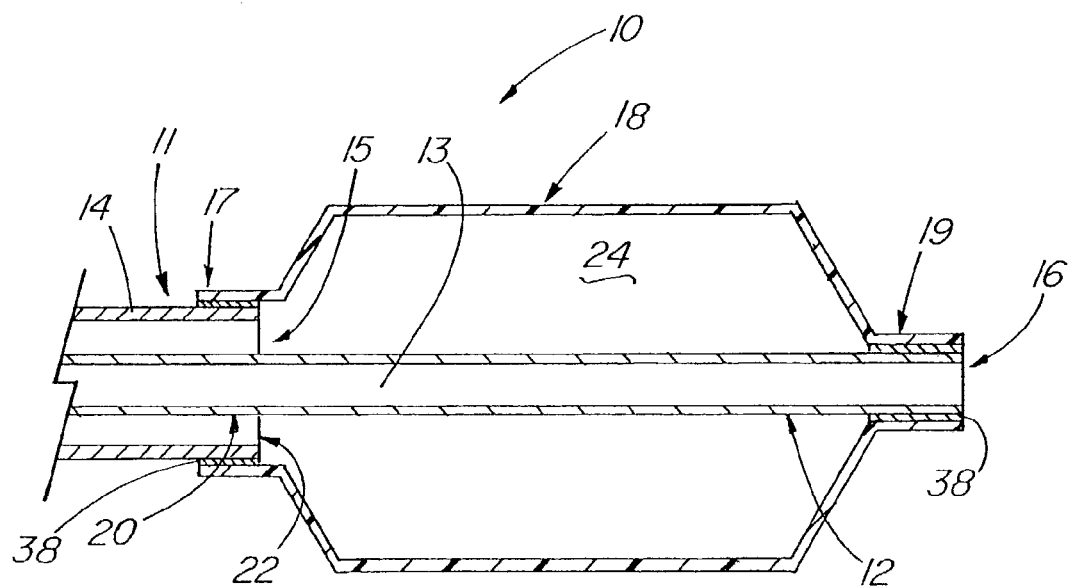
FIG. 1 is a partial cross-sectional view of the medical device of the preferred embodiment of the present invention.

With reference first to FIG. 1, an embodiment of a medical device according to the present invention is thereshown, useful for dilating a narrowing or obstruction in a vessel or lumen in a patient, and/or for deploying a stent (not shown in the Figures) across the site of such a narrowing or obstruction to prevent its restenosis. The medical device 10 of the present invention first comprises a catheter shaft 11. The catheter shaft 11 is preferably a multi-element shaft, and preferably comprises an inner catheter shaft 12 received in and extending longitudinally through a lumen 20 in an outer catheter shaft 14. The catheter shaft 11 could alternatively comprise a single catheter shaft (not shown) having at least one lumen formed longitudinally therein. The inner and outer catheter shafts 12 and 14 preferably comprise medical grade polyethylene, polyamide or other suitable medical grade materials, and are of a diameter or French size suited to the particular procedure in which it is intended to use the device 10. The inner and outer catheter shafts 12 and 14 can comprise the same or different such materials.

The device 10 of the present invention also comprises an inflatable balloon 18 carried on the catheter shaft 11. The balloon 18 comprises an irradiation cross-linked mixture of a polyamide elastomer and at least one additional cross-linking reactant, the nature of the mixture and its cross-linking being described in more detail below. The balloon 18 is dimensioned and adapted for the particular procedure in which it is to be employed. Balloon length and inflation diameters suited to various procedures are well known, and for brevity need not be recited here.

The balloon 18 is preferably formed separately from the catheter shaft 11, and separately from the inner and outer catheter shafts 12 and 14. The balloon 18 is more preferably affixed at its proximal end 17 to the distal end 15 of the outer catheter shaft 14, and at its distal end 19 to the distal end 16 of the inner catheter shaft 12. Affixing can occur by use of a suitable medical grade adhesive 38, or by thermal bonding.

The lumen 20 defined in the outer shaft 14 permits the supply of an inflation fluid from a supply (not shown) and to the interior 24 of the balloon 18. More particularly, the catheter shaft 14 has a lumen end port 22 defined at its distal end 15, placing the balloon interior 24, the catheter shaft lumen 20 and the inflation fluid supply in fluid communication with one another. The balloon 18 may carry on it a stent of conventional design (not shown), expanded or permitted to expand upon inflation of the balloon 18.

Either or both of the inner and outer catheter shafts 12 and 14 can include one or more other lumens for any of a variety of conventional purposes. For example, the inner catheter shaft 12 can include a lumen 13 defined longitudinally therein for the introduction or passage of a conventional wire guide therethrough. In use of the medical device 10 of the present invention, this wire guide would first be advanced across the narrowing or obstruction to be treated, and the balloon 18 of the medical device 10 then advanced along this wire guide until the balloon 18 was positioned across the narrowing or obstruction. Inflation of the balloon 18 then widens the narrowing or obstruction. If the medical device 10 has been supplied with a stent, such inflation deploys the stent at the site of the narrowing or obstruction, preventing restenosis of the site. Of course, any additional lumens in the inner and outer catheter shafts 12 and 14 can be employed for other conventional purposes, such as fluid drainage or injection, or the passage of another catheter or other medical device or instrument.

As indicated above, the balloon 18 comprises an irradiation cross-linked mixture of a polyamide elastomer and at least one additional cross-linking reactant which acts to covalently link the chains of the polyamide elastomer. The polyamide elastomer can be a polyester amide, a polyether ester amide or a polyether amide. Specific commercial examples of such materials include ESTAMID®, PEBAX®, VESTAMID®, GRILAMID® and GRILON® brand polymers. The polyamide elastomer used to make the balloon 18 is preferably a nylon block copolymer. Nylon block copolymers expected to be useful in making the balloon 18 of the medical device 10 of the present invention include polyamide blocks separated by polyether blocks or other elastomeric blocks or segments, such as polyesters, hydrocarbons or polysiloxanes. Preferably, the polyamide elastomer is an polyester amide, a polyether ester amide or a polyether amide as described above. More preferably, the nylon block copolymer employed in the mixture from which the balloon 18 is formed comprises a nylon block copolymer including polyamide blocks separated by polyether blocks. Most preferably, the nylon block copolymer is PEBAX® brand nylon block copolymer. Although probably not preferred, the mixture from which the balloon 18 of the medical device 10 of the present invention can also comprise a minor proportion (less than 50 percent by weight or mole fraction) of a second polyamide elastomer or another polyamide (such as nylon) similarly capable of being cross-linked by the at least one additional cross-linking reactant.

The at least one additional cross-linking reactant can comprise any of a variety of materials. For example, the at least one additional cross-linking reactant can comprise a difunctional material selected from the class consisting of diallyl adipate; diallyl carbonate; diallyl maleate; diallyl succinate; diallyl tetrabromophthalate; diethyl diallylmalonate; dimethyl diallylmalonate; and 2,2,6,6-tetrabromobisphenol A diallyl ether. The mixture from which the balloon 18 is formed preferably comprises about 1 to about 2 percent by weight of such a difunctional material. Alternatively, the at least one additional cross-linking material can comprise a trifunctional material selected from the class consisting of 2,5-diallyl-4,5-dimethyl-2-cyclopenten-1-one; diallyl fumarate; diallyl itaconate; 1,3,5-triallyl-2-methoxybenzene; triallyl trimesate (triallyl 1,3,5-benzenetricarboxylate); triallyl trimellitate (triallyl 1,2,4-benzenetricarboxylate); and pentaerythritol triallyl ether. The mixture from which the balloon 18 is formed then preferably comprises about 0.5 to about 1.5 percent by weight of such a trifunctional material. The amount of trifunctional material required for the balloon 18 will likely be somewhat less than the amount of difunctional material required, because the additional functional group of the trifunctional material provides an additional site for the material to bond to the chains of the polyamide elastomer. The at least one additional cross-linking reactant can alternatively comprise a tetrafunctional material selected from the class consisting of tetraallyl cis,cis,cis,cis-cyclopentane-1,2,3,4-tetracarboxylate; and N,N,N',N'-tetraallylethylenediamine. The mixture from which the balloon 18 is formed then preferably comprises about 0.01 to about 1 percent by weight of the tetrafunctional material. The dramatically lower value is possible because the fourth functional group may permit crosslinking to be achieved even more readily than with trifunctional materials; however, depending upon the sterics of the particular polyamide elastomer and the particular tetrafunctional material selected, such low values may not actually be enjoyed. The at least one additional cross-linking reactant can instead comprise an aromatic molecule containing at least two ring substituents, each of the ring substituents having labile hydrogens at a benzylic site therein. The mixture from which the balloon 18 is formed then preferably comprises about 0.5 to about 1.5 percent by weight of the aromatic molecule containing at least two ring substituents, each of the ring substituents having labile hydrogens at a benzylic site therein. The aromatic molecule containing at least two ring substituents, each of the ring substituents having labile hydrogens at a benzylic site therein, is preferably selected from the class consisting of 1,3,5 triethyl benzene; 1,2,4 triethyl benzene; and 1,3,5 triisopropyl benzene. As indicated above, the aromatic molecule containing at least two ring substituents, each of the ring substituents having labile hydrogens at a benzylic site therein, may instead be any of a wide variety of suitably-substituted aromatic molecules; these three are preferred because they are commercially available at the present time. Finally, the at least one additional cross-linking reactant can comprise no more than about 1.5 percent by weight of triallyl cyanurate or triallyl isocyanurate, or about 1 to about 2 percent by weight of diallyl phthalate or meta-phenylene dimaleimide.

Without regard to the particular at least one additional cross-linking reactant employed, the mixture from which the balloon 18 is formed comprises an amount of the at least one additional cross-linking reactant sufficient to give the balloon 18 a strength generally about equal to, and in some cases perhaps greater than, that of a balloon composed of the polyamide elastomer and comparably cross-linked by irradiation, but in the absence of any cross-linking reactant, agent or promoter.

The mixture is preferably irradiated before the balloon 18 is formed by inflation as described below, or otherwise formed. The mixture of the polyamide elastomer and the at least one additional cross-linking reactant can be cross-linked by irradiation with an electron beam or with ultraviolet, X- or gamma rays, preferably with an electron beam since it may be more efficient and may achieve satisfactory cross-linking at lower fluences than the others. Preferably, the mixture is cross-linked by exposure to a total fluence of about 0.5 to about 20 megarads.

The general process for forming a balloon 18 from the mixture of the polyamide elastomer and the at least one additional cross-linking reactant, and incorporating such a balloon into a medical device 10, can now be readily understood. A familiarity with the principles of manufacturing balloons for medical devices and the associated FDA requirements is presumed. Those skilled in the art of manufacturing balloons for medical devices should readily be able to adapt the general process described herein to the particular materials being employed.

In its simplest form, the process for assembling a medical device comprising an expandable balloon 18 comprises the steps of creating a mixture of a polyamide elastomer and at least one additional cross-linking reactant as described above; cross-linking the mixture of the polyamide elastomer and the at least one additional cross-linking reactant by exposing the mixture to a suitable fluence of radiation; and forming the resulting cross-linked mixture into the balloon 18. The details of the preferred composition of the nylon block copolymer and the at least one additional cross-linking reactant, as well as the preferred types and fluences of irradiation, are recited above; for brevity, these will not be repeated.

Figure 3:
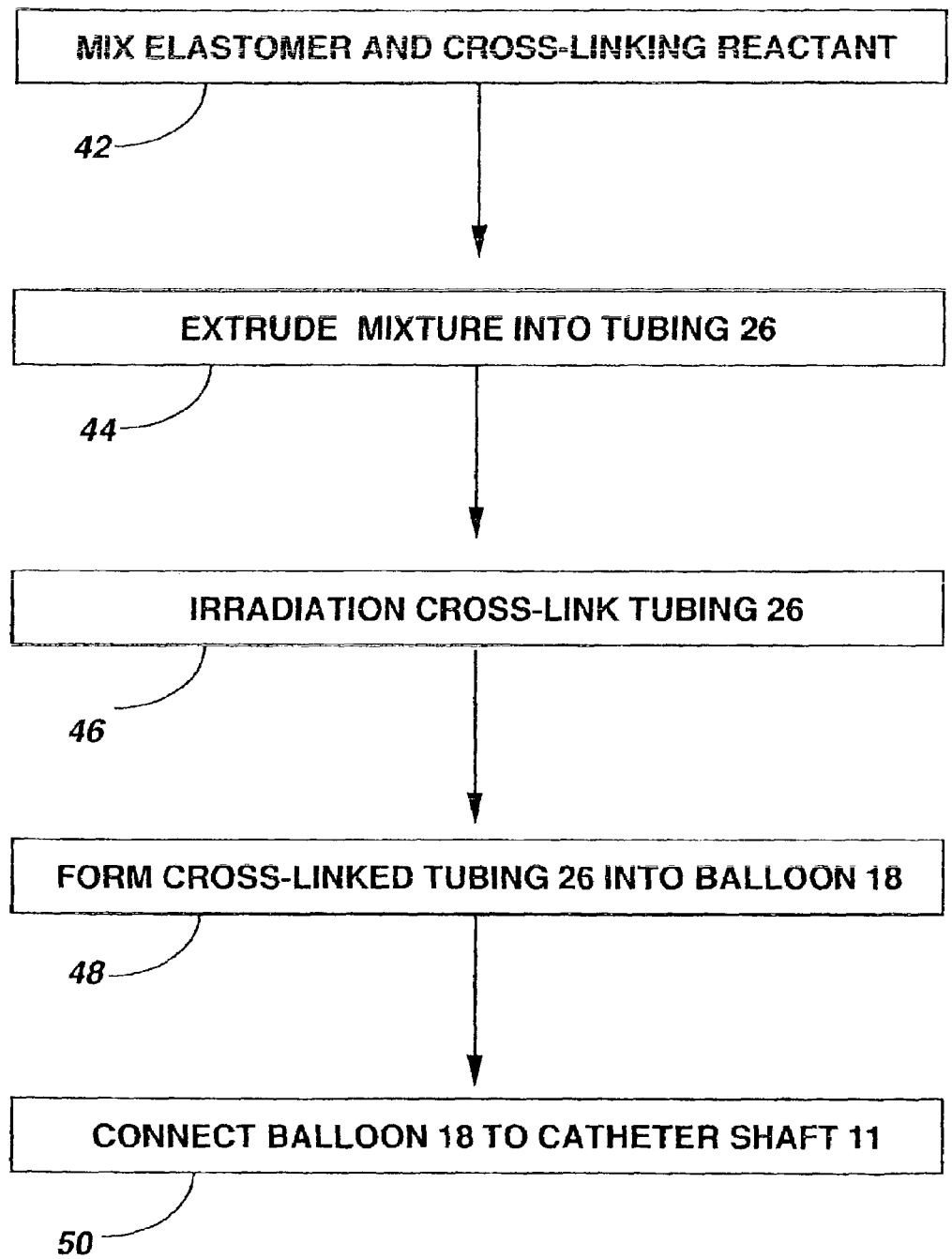
FIG. 3 is a flow chart of the process of assembling the medical device of the preferred embodiment of the present invention.

The process of the present invention can be carried out with any of a variety of specific process steps known to be useful for assembling balloon-type medical devices from materials other than the specific mixtures of polyamide elastomers and cross-linking reactants disclosed herein. Accordingly, the description of any particular steps or any specific apparatus for performing any particular steps should not be taken as limiting the scope of the broad process disclosed herein. For purposes of illustration, however, a preferred process according to the present invention for assembling the medical device 10 is shown in the flow chart of FIG. 3. First, the polyamide elastomer and the at least one additional cross-linking reactant are intimately mixed together (box 42). Such mixing is most conveniently carried out by compounding and/or blending the elastomer and the cross-linking reactant together. Next, the mixture of the polyamide elastomer and the at least one additional cross-linking reactant are formed into a shape suitable for irradiation and further processing. Conveniently, the mixture of the elastomer and the cross-linking reactant are extruded into the shape of a tubing 26 (box 44). Other extrusion shapes can be employed as needed or desired. The tubing 26 (or other form of the mixture) is then irradiated to cross-link the material (block 46). Irradiation is most conveniently carried out by exposing the tubing 26 to an electron beam or to a source of ultraviolet, X- or gamma rays, the electron beam probably being preferred.

Figure 2:
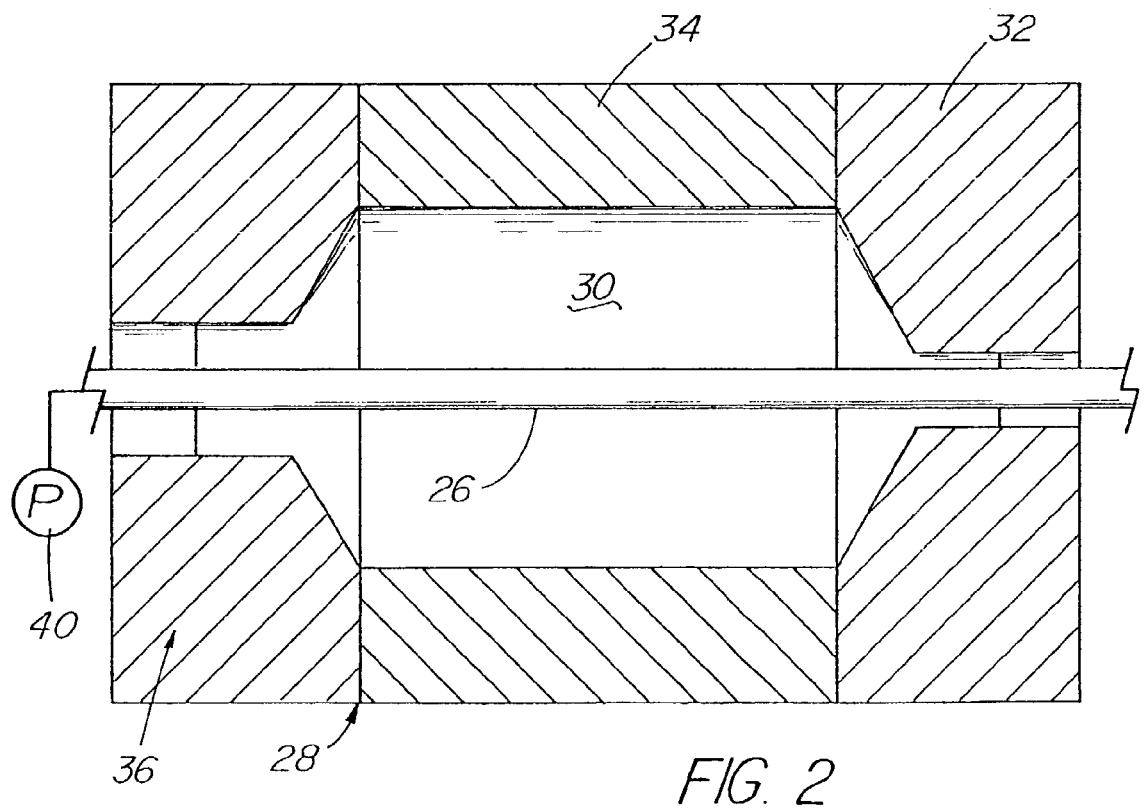
FIG. 2 is a partial cross-sectional view of a step in the process for assembling the medical device of the preferred embodiment of the present invention.

The cross-linked material, in the physical form of the tubing 26, is then formed into the balloon 18 (box 48). The tubing 26 is most conveniently formed into the balloon 18 by applying heat and an inflation medium or fluid to the tubing 26. A simplified view of an apparatus for performing this balloon-forming step is shown in FIG. 2. The tubing 26 is introduced into a heatable mold 28 having first, second and third mold parts 32, 34 and 36, whose facing surfaces define between them a mold cavity 30. The mold cavity is shaped and sized substantially the same as the ultimately desired shape and size of the balloon 18, shrinkage and other conventional molding concerns having been taken into account. The mold 28 is heated, thereby warming the tubing 26, and a source 40 of pressurized inflation medium is applied to an open end of the tubing 26 outside the mold 28. Sufficient inflation pressure is supplied from the source 40 to cause the tubing 26 to expand within the mold 28 until the tubing 26 contacts the facing surfaces of the mold parts 32, 34 and 36, and takes on the shape of the mold cavity 30. Pressure in the tubing 26 is then relieved, the tubing 26 deflated and removed from or allowed to exit the mold 28 for further processing as needed. Stretching of the tubing 26 and/or repeated heating or inflation of the tubing 26 can be performed in the conventional manner, as needed or as desired to achieve the balloon 18 (as a portion of the tubing 26).

Once the balloon 18 is formed as a part of the tubing 26, the balloon 18 is cut from the tubing 26 and connected to the catheter shaft 11 (box 50), for example, by affixing the proximal and distal ends 17 and 19 of the balloon 18 to the distal ends 16 and 15 of the inner and outer catheter shafts 12 and 14. Affixing can be carried out by use of the medical grade adhesive 38 described above, or by heat bonding.

The process of the present invention forming the medical device is of course not limited to the particular steps described above. A wide variety of steps and methods for forming medical device balloons from other materials are well-known, and are expected to be useful in the assembly of the medical device 10. For example, molds having other than three pieces can be used; indeed, a single balloon for a medical device can be formed with no mold at all, just inflation of a parison having only an inlet for an inflation fluid, and no outlet.

EXAMPLES

A variety of examples of irradiation cross-linked mixtures of PEBAX® brand nylon block copolymer with differing amounts of triallyl cyanurate or triallyl isocyanurate as the at least one cross-linking reactant are disclosed in Tables 1 through 4 annexed hereto. The French size indicates the size of the tubing 26 from which the balloon 18 is made, while the Double Wall (in inches) indicates the wall thickness of the balloon 18 ultimately formed. In the Material Formulations column in the Tables, 7233SAO1 and 6333SNO1 refer to two different grades of PEBAX® brand copolymers. Formulations containing both grades thus constitute mixtures of two different copolymers. The particular nylon block copolymer mixtures used in the examples were specially ordered mixtures, mixtures which it is believed are not otherwise commercially distributed at this time. More specifically, it is believed that Foster Corporation, Dayville, Conn., commercially distributes (under the trade name FOSTALINK™) mixtures containing PEBAX® brand copolymer and 2 percent or more by weight of either triallyl cyanurate or triallyl isocyanurate. Mixtures containing 0.125 to 1.00 percent weight of either triallyl isocyanurate or triallyl isocyanurate were requested from Foster Corporation, and were used in the examples in the Tables. As an aside, it should be noted that it is not presently known which of the two materials, the triallyl cyanurate or the triallyl isocyanurate, was included in the FOSTALINK™ materials used in the examples.

A number of comparative examples are shown in the Tables, in which the triallyl cyanurate or triallyl isocyanurate is not present; in which the mixture of the nylon block copolymer and the at least one additional cross-linking reactant is not irradiated; in which the at least one additional cross-linking reactant is omitted; and in which nylon 12 is added to the nylon block copolymer at an indicated percentage by weight. Irradiation at the indicated fluence occurred by exposure to an electron beam; as indicated above, other forms of irradiation are expected to be less efficient than electron beam at performing the cross-linking desired in the present invention, and higher fluences of ultraviolet, X- or gamma rays may be required to achieve the same results.

Table 1 contains comparative examples of mixtures (Material Formulations) employed to form tubing of the indicated French size and diameters into balloons. Except for the last entry (which comprised solely nylon 6/6), the comparative examples of Table 1 were carried out with mixtures comprising a PEBAX® brand nylon block copolymer and 2 or 3 percent by weight of a triallyl cyanurate or triallyl isocyanurate; mixtures comprising a PEBAX® brand nylon block copolymer, 3 percent by weight of a triallyl cyanurate or triallyl isocyanurate and 10 percent by weight of a nylon 12; or mixtures comprising a PEBAX® brand nylon block copolymer and 10 percent by weight of a nylon 12, without any triallyl cyanurate or triallyl isocyanurate.

Table 2 contains comparative examples of mixtures comprising a nylon 12 with no cross-linking reagent; a PEBAX® brand nylon block copolymer with no cross-linking reagent; and a PEBAX® brand nylon block copolymer with 2 percent by weight of a triallyl cyanurate or triallyl isocyanurate, as well as mixtures containing 3 percent by weight of a triallyl cyanurate or triallyl isocyanurate and further including a second PEBAX® brand nylon block copolymer or a nylon 12.

Table 3 contains further comparative examples of such mixtures.

Finally, Table 4 contains examples of mixtures useful for forming the balloon 18 of the medical device 10 of the present invention. More particularly, the mixtures of the examples shown in Table 4 comprise a PEBAX® brand nylon block copolymer and 0.125 to 1.00 percent by weight of a triallyl cyanurate or triallyl isocyanurate, irradiated by electron beam at total fluences of 0.5 to 7 megarads (comparative examples at 0.0 megarads also being included in Table 4).

It is believed that the data in Tables 1 through 4 demonstrate that a medical device 10 of the present invention, incorporating a balloon 18 comprising an irradiated mixture of a polyamide elastomer and at least one additional cross-linking reactant as defined herein, possesses significant advantages over prior medical devices incorporating balloons made of other materials. The present invention thus provides a medical device 10 which is particularly useful for dilating a narrowing or obstruction in a vessel or lumen in a patient, and for deploying a stent across the site of such a narrowing or obstruction to prevent its restenosis. The balloon 18 of the device 10 of the present invention has generally improved strength (for example, greater tensile strength, burst pressure and/or puncture resistance) in comparison to balloons in prior devices for these purposes, while simultaneously possessing acceptable compliance. Gelling during the steps leading to manufacture of the balloon 18, if present, is limited to an acceptable level. The balloon 18 of the medical device 10 of the present invention is made from materials which meet a variety of desirable processing criteria, including thermal stability, non-toxicity, non-volatility, high boiling point (preferably, solid at room temperature), high flash point, insensitivity to moisture and commercial availability.

By way of non-limiting example, a particularly preferred process for forming a medical device balloon includes the following steps. First, a blend of PEBAX® 7233 and 1 percent by weight triallyl isocyanurate (as the additional cross-linking reactant) is extruded in the form of a tubing of desired diameter. The extruded tubing blend is then exposed to 3 megarads of irradiation via electron beam. The ends of the tubing are drawn or stretched to a reduced diameter, while a central portion between the ends of the tubing is left undrawn or unstretched, this central portion of the tubing being the portion from which the balloon 18 is blown. The tubing is then introduced into a mold and preliminarily heated to about 135° F. to about 150° F., then subjected to a blow pressure of about 350 psi to about 650 psi and a blow temperature of about 200° F. to about 250° F. The temperature of the mold is then raised by about 30° F. for about 30 sec to about 60 sec, to further set or cure the blown material. The mold is cooled and the blown material removed from the mold. The central, undrawn portion constitutes the balloon 18, and is cut from the tubing and mounted to the catheter shaft 11 in a suitable manner. The times, pressures and temperatures of this non-limiting example depend, of course, upon the thickness and inner diameter of the partially drawn tubing; those skilled in the art of medical balloon manufacture should be well capable of varying these conditions to yield a suitable balloon from any particular initial material blend.

The details of the construction or composition of the various elements of the medical device 10 of the present invention not otherwise disclosed are not believed to be critical to the achievement of the advantages of the present invention, so long as the elements possess the strength or mechanical properties needed for them to perform as disclosed. The selection of any such details of construction are believed to be well within the ability of one of even rudimentary skills in this area, in view of the present disclosure. For practical reasons, however, the medical devices 10 of the present invention should probably be considered to be single-use devices, rather than being reusable.

INDUSTRIAL APPLICABILITY

The present invention is useful for dilating a narrowing or obstruction in a vessel or lumen in a patient, and for deploying a stent across the site of such a narrowing or obstruction to prevent its restenosis, and therefore finds applicability in human and veterinary medicine.

It is to be understood, however, that the above-described device is merely an illustrative embodiment of the principles of this invention, and that other devices and methods for using them may be devised by those skilled in the art, without departing from the spirit and scope of the invention. It is also to be understood that the invention is directed to embodiments both comprising and consisting of the disclosed parts.

TABLE 1

| Parison French size (O.D.) | Material Desc. | Vendor Mat'l. Lot # | Lot # | Mat'l. Formulation | Avg. Tensile (lb.) | Std Dev | Elongation | Std. Dev |
|---|---|---|---|---|---|---|---|---|
| 4.7 | R&D1102 | S66246 | P136575 | 7233SAO1 w/2% XL | 10.515 | 1.20 | 7.69 | 1.095 |
| 4.7 | R&D1102 | S66246 | P136575 | 7233SAO1 w/2% XL | 9.708 | 1.11 | 7.241 | 0.916 |
| 6.1 | R&D1102 | S66246 | P136573 | 7233SAO1 w/2% XL | 17.575 | 1.218 | 7.785 | 0.594 |
| 3.4 | R&D1102 | S66246 | P136573 | 7233SAO1 w/2% XL | 16.725 | 1.48 | 6.943 | 0.672 |
| 3.4 | R&D1137 | S68043 | P137420 | 7233SAO1 w/3% XL | 12.054 | 0.537 | 12.561 | 0.697 |
| 3.4 | R&D1137 | S68043 | P137420 | 7233SAO1 w/3% XL | 10.5 | 0.786 | 7.84 | 0.829 |
| 3.4 | R&D1137 | S68043 | P137420 | 7233SAO1 w/3% XL | 10.6 | 0.757 | 7.60 | 0.609 |
| 5.5 | R&D1137 | S68043 | P137420 | 7233SAO1 w/3% XL | 10.6 | 0.757 | 7.60 | 0.609 |
| 5.5 | R&D1137 | S68043 | P137423 | 7233SAO1 w/3% XL | 21.508 | 1/846 | 11.541 | 0.721 |
| 5.5 | R&D1137 | S68043 | P137423 | 7233SAO1 w/3% XL | 20.549 | 1.646 | 7.65 | 0.831 |
| 5.5 | R&D1137 | S68043 | P137423 | 7233SAO1 w/3% XL | 18.948 | 1.055 | 7.69 | 0.733 |

TABLE 1-continued

| 5.5 | R&D1137 | S68043 | P137423 | 7233SAO1 w/3% XL | 20.072 | 1.185 | 7.50 | 0.658 |
|---|---|---|---|---|---|---|---|---|
| 5.5 | R&D1137 | S68043 | P138587 | 7233SAO1 w/3% XL | 28.39 | 2.143 | 13.908 | 1.113 |
| 5.5 | R&D1137 | S68043 | P138587 | 7233SAO1 w/3% XL | 27.893 | 2.179 | 10.382 | 0.952 |
| 5.5 | R&D1137 | S68043 | P138587 | 7233SAO1 w/3% XL | 25.766 | 1.73 | 9.237 | 0.727 |
| 5.5 | R&D1137 | S68043 | P138587 | 7233SAO1 w/3% XL | 25.766 | 1.73 | 9.237 | 0.727 |
| 5.5 | R&D1137 | S68043 | P138587 | 7233SAO1 w/3% XL | 25.766 | 1.73 | 9.237 | 0.727 |
| 5.5 | R&D1137 | S68043 | P138587 | 7233SAO1 w/3% XL | 26.642 | 2.385 | 9.319 | 0.947 |
| 5.5 | R&D1137 | S68043 | P138587 | 7233SAO1 w/3% XL | 22.977 | 2.01 | 7.533 | 0.753 |
| 5.5 | R&D1137 | S68043 | P138587 | 7233SAO1 w/3% XL | 22.311 | 1.69 | 6.751 | 0.564 |
| 5.5 | R&D1137 | S68043 | P138587 | 7233SAO1 w/3% XL | 19.907 | 0.976 | 5.213 | 0.284 |
| 5.5 | R&D1137 | S68043 | P138587 | 7233SAO1 w/3% XL | 19.08 | 1.392 | 4.689 | 0.425 |
| 5.5 | R&D1137 | S68043 | P138587 | 7233SAO1 w/3% XL | 17.714 | 0.817 | 3.466 | 0.228 |
| 5.5 | R&D1138 | S68541 | P138614 | 10% PA12/86.5% 723SAO1 /3% XL | 26.639 | 1.379 | 12.414 | 0.736 |
| 5.5 | R&D1138 | S68541 | P138614 | 10% PA12/86.5% 723SAO1 /3% XL | 22.232 | 0.477 | 7.97 | 0.497 |
| 5.5 | R&D1138 | S68541 | P138614 | 10% PA12/86.5% 723SAO1 /3% XL | 22.612 | 1/--1 | 8.273 | 0.552 |
| 5.5 | R&D1138 | S68541 | P138614 | 10% PAl2/86.5% 723SAO1 /3% XL | 20.807 | 1.229 | 7.06 | 0.691 |
| 5.5 | R&D1138 | S68541 | P138614 | 10% PA12/86.5% 723SAO1 /3% XL | 19.537 | 1/1-0 | 5.882 | 0.432 |
| 5.5 | R&D1138 | S68541 | P138614 | 10% PA12/86.5% 723SAO1 /3% XL | 18.44 | 1.286 | 4.872 | 0.544 |
| 5.5 | R&D1138 | S68541 | P138614 | 10% PA12/86.5% 723SAO1 /3% XL | 13.388 | 0.804 | 1.585 | 1.332 |
| 5.5 | R&D1157 | S68541 | P138591 | 7233SAO1 x/ 10% PA12 | 19.372 | 0.29 | 8.635 | 0.191 |
| 5.5 | R&D1157 | S68541 | P138591 | 7233SAO1 x/ 10% PA12 | 18.732 | 0.348 | 8.082 | 0.326 |
| 5.5 | R&D1157 | S68541 | P138591 | 7233SAO1 x/ 10% PA12 | 18.831 | 1.203 | 8.358 | 0.657 |
| 5.5 | R&D1157 | S68541 | P138591 | 7233SAO1 x/ 10% PA12 | 19.939 | 0.779 | 8.294 | 0.459 |
| 5.5 | R&D1157 | S68541 | P138591 | 7233SAO1 x/ 10% PA12 | 17.404 | 0.71 | 7.569 | 0.491 |
| 5.5 | R&D1157 | S68541 | P138591 | 7233SAO1 x/ 10% PA12 | 15.692 | 0.858 | 5.476 | 0.395 |
| 5.5 | R&D1157 | S68541 | P138591 | 7233SAO1 x/ 10% PA12 | 12.152 | 0.541 | 1.447 | 2.057 |
| 5.5 | 40080 | S64330 | P138669 | Nyton 6/6 0% XL | 38.336 | 2.134 | 11.577 | 0.773 |

| Parison French size (O.D.) | Nominal Preaaure (atm) | Mrad | Nominal Ballon Diameter (mm) | Compliance (mm/atm) | Avg. Burst (atm) | Std. Dev (atm) | Double Wall (in) | Mean Burst Diameter (mm) |
|---|---|---|---|---|---|---|---|---|
| 4.7 | 3 | 5 | 6.00 | 0.14 | 10.1 | 0.78 | 0.00125 | 6.75 |
| 4.7 | 3 | 7 | 6.00 | 0.12 | 9.97 | 0.78 | 0.00125 | 8.8 |
| 6.1 | | 5 | 6.00 | | | | | |
| 3.4 | | 7 | 6.00 | | | | | |
| 3.4 | | 0 | 6.00 | | | | | |
| 3.4 | | 2.5 | 4.00 | | | | | |
| 3.4 | 11.5 | 4 | 4.00 | 0.04 | 25 | 1.83 | 0.002 | 3.36 |
| 5.5 | 11 | 4 | 4.00 | 0.036 | 26.2 | 1.58 | 0.002 | 3.36 |
| 5.5 | | 0 | 4.00 | 0.21 | 13.2 | 0.4 | 0.00175 | 7.94 |
| 5.5 | | 3 | 6.00 | 0.09 | 14.8 | 1 | 0.00225 | 6.54 |
| 5.5 | | 5 | 6.00 | 0.083 | 15.4 | 0.9 | 0.00225 | 6.5 |
| 5.5 | | 8 | 6.00 | 0.088 | 15.39 | 1.18 | 0.0025 | 6.51 |
| 5.5 | 3 | 0 | 6.00 | 0.215 | 15.6 | 0.5 | 0.002 | |
| 5.5 | 7 | 3 | 6.00 | 0.085 | 16.2 | 2.8 | 0.0025 | 7.00 |
| 5.5 | 8 | 5 | 6.00 | 0.075 | 18.5 | 1.95 | 0.0025 | 6.68 |
| 5.5 | 8 | 5 | 6.00 | 0.069 | 19.05 | 1.17 | 0.0025 | 6.63 |
| 5.5 | 7 | 5 | 6.00 | 0.052 | 20.29 | 1.3 | 0.0025 | 6.61 |
| 5.5 | 9 | 7 | 6.00 | 0.079 | 19.9 | 0.95 | 0.0025 | 6.95 |
| 5.5 | | 15 | 6.00 | | | | | |
| 5.5 | | 25 | 6.00 | | | | | |
| 5.5 | | 50 | 6.00 | | | | | |
| 5.5 | | 75 | 6.00 | | | | | |
| 5.5 | | 100 | 6.00 | | | | | |
| 5.5 | | 0 | 6.00 | | | | | |
| 5.5 | | 3 | 6.00 | | | | | |
| 5.5 | 10 | 5 | 6.00 | 0.065 | 17.6 | 2.5 | 0.003 | 6.31 |
| 5.5 | | 7 | 6.00 | | | | | |
| 5.5 | | 15 | 6.00 | | | | | |
| 5.5 | | 25 | 6.00 | | | | | |
| 5.5 | | 100 | 6.00 | | | | | |
| 5.5 | 3 | 3 | 6.00 | 0.19 | 15.73 | 0.451 | 0.002 | 8.74 |
| 5.5 | 3 | 5 | 6.00 | 0.253 | 15.7 | 0.46 | 0.00225 | 9.01 |
| 5.5 | 3 | 7 | 6.00 | 0.173 | 14.81 | 0.528 | 0.0015 | 8.43 |
| 5.5 | 3 | 15 | 6.00 | 0.189 | 13.23 | 0.483 | 0.0015 | 8.35 |
| 5.5 | | 25 | 6.00 | | | | | |
| 5.5 | | 50 | 6.00 | | | | | |
| 5.5 | | 100 | 6.00 | | | | | |
| 5.5 | | 0 | 6.00 | | | | | |

TABLE 2

| Parison French size (O.D.) | Material Desc. | Vendor Mat'l. Lot # | Lot # | Mat'l. Formulation | Avg. Tensile (lb.) | Std. Dev | Elongation | Std. Dev |
|---|---|---|---|---|---|---|---|---|
| 5.5 | 40140 | S68802 | P138661 | Nylon 12 0% XL | 22.116 | 0.84 | 7.841 | 0.459 |
| 5.8 | R&D1102 | S66246 | P139014 | 7233SAO1 w/2% XL | 27.313 | 0.701 | 13.113 | 0.426 |
| 5.8 | R&D1102 | S66246 | P139014 | 7233SAO1 w/2% XL | 25.482 | 1.427 | 9.972 | 0.638 |
| 5.8 | R&D1102 | S66246 | P139014 | 7233SAO1 w/2% XL | 24.93 | 1.547 | 9.32 | 0.738 |
| 5.8 | R&D1102 | S66246 | P139014 | 7233SAO1 w/2% XL | 24.93 | 1.547 | 9.32 | 0.738 |
| 5.8 | R&D1102 | S66246 | P139014 | 7233SAO1 w/2% XL | 24.93 | 1.547 | 9.32 | 0.738 |
| 5.8 | R&D1102 | S66246 | P139014 | 7233SAO1 w/2% XL | 24.93 | 1.547 | 9.32 | 0.738 |
| 5.8 | R&D1102 | S66246 | P139014 | 7233SAO1 w/2% XL | 23.226 | 1.488 | 8.371 | 0.501 |
| 5.8 | R&D1102 | S66246 | P139014 | 7233SAO1 w/2% XL | 20.757 | 1.604 | 6.963 | 0.625 |
| 5.8 | R&D1102 | S66246 | P139014 | 7233SAO1 w/2% XL | 20.75 | 0.951 | 6.84 | 0.35 |
| 5.8 | R&D1102 | S66246 | P139014 | 7233SAO1 w/2% XL | 19.3 | 0.86 | 5.645 | 0.357 |
| 5.8 | R&D1102 | S66246 | P139014 | 7233SAO1 w/2% XL | 16.612 | 0.875 | 3/792 | 0.175 |
| 5.8 | R&D1138/41130 | S68541/S59677 | P138892 | 10% PA12/86.5% 7233SAO1/3% XL | 33.929 | 1.75 | 15.984 | 0.822 |
| 5.8 | R&D1138/41130 | S68541/S59677 | P138892 | 10% PA12/86.5% 7233SAO1/3% XL | 25.412 | 2.563 | 9.424 | 0.851 |
| 5.8 | R&D1138/41130 | S68541/S59677 | P138892 | 10% PA12/86.5% 7233SAO1/3% XL | 24.227 | 2.081 | 9.287 | 0.849 |
| 5.8 | R&D1138/41130 | S68541/S59677 | P138892 | 10% PA12/86.5% 7233SAO1/3% XL | 23.907 | 1.344 | 8.827 | 0.524 |
| 5.8 | R&D1138/41130 | S68541/S59677 | P138892 | 10% PA12/86.5% 7233SAO1/3% XL | 22.803 | 1.748 | 8.245 | 0.653 |
| 5.8 | R&D1138/41130 | S68541/S59677 | P138892 | 10% PA12/86.5% 7233SAO1/3% XL | 22.024 | 0.752 | 0.385 | 0.385 |
| 5.5 | 44130 | S59677 | P138180 | 7233SNO1 | | | | |
| 5.5 | 44130 | S59677 | P138180 | 7233SNO1 | 19.581 | 0.735 | 0.719 | 0.719 |
| 5.5 | 44130 | S59677 | P138180 | 7233SNO1 | 18.986 | 0.494 | 0.478 | 0.478 |
| 5.5 | 44130 | S59677 | P138180 | 7233SNO1 | 17.168 | 0.996 | 0.926 | 0.926 |
| 5.5 | 44130 | S59677 | P138180 | 7233SNO1 | 15.886 | 0.915 | 0.483 | 0.483 |
| 5.5 | 44130 | S59677 | P138180 | 7233SNO1 | 14.582 | 0.473 | 0.207 | 0.207 |
| 5.5 | 44130 | S59677 | P138180 | 7233SNO1 | 13.545 | 0.762 | 0.5 | 0.5 |
| 5.5 | 44130 | S59677 | P138180 | 7233SNO1 | 12.192 | 0.682 | 0.216 | 0.216 |
| 6.2 | R&D 1137 | S68043 | P137426 | 7233SAO1 w/3% XL | 30.464 | 1.361 | 0.595 | 0.595 |
| 6.2 | R&D 1137 | S68043 | P137426 | 7233SAO1 w/3% XL | 25.773 | 1.341 | 0.0414 | 0.414 |
| 6.2 | R&D 1137 | S68043 | P137426 | 7233SAO1 w/3% XL | 25.235 | 2.492 | 0.835 | 0.835 |
| 6.2 | R&D 1137 | S68043 | P137426 | 7233SAO1 w/3% XL | 24.405 | 1.366 | 0.409 | 0.409 |
| 6.2 | R&D 1138 | S68042 | P137432 | 7233SAO1 w/10% PA12w/3% XL | 27.116 | 1.659 | 0.656 | 0.656 |
| 6.2 | R&D 1138 | S68042 | P137432 | 7233SAO1 w/10% PA12w/3% XL | 26.495 | 1.809 | 0.504 | 0.504 |
| 6.2 | R&D 1138 | S68042 | P137432 | 7233SAO1 w/10% PA12w/3% XL | 24.552 | 1.585 | 0.491 | 0.491 |
| 6.2 | R&D 1138 | S68042 | P137432 | 7233SAO1 w/10% PA12w/3% XL | 23.852 | 1.925 | 0.625 | 0.625 |
| 6.2 | R&D 1138 | S66758/S68042 | P137433 | 6333SNO1 + 7233SAO1 W/10% PA12x/3% XL | 29.92 | 2.724 | 1.265 | 1.265 |
| 6.2 | R&D 1138 | S66758/S68042 | P137433 | 6333SNO1 + 7233SAO1 W/10% PA12x/3% XL | 25.196 | 2.647 | 1.177 | 1.177 |
| 6.2 | R&D 1138 | S66758/S68042 | P137433 | 6333SNO1 + 7233SAO1 W/10% PA12x/3% XL | 23.244 | 2.8206 | 1.444 | 1.444 |

| Parison French size (O.D.) | Norminal Pressure (atm) | Mrad | Nominal Balloon Diameter (mm) | Compliance (mm/atm) | Avg. Burst (atm) | Std. Dev (atm) | Double Wall (in) | Mean Burst Diameter (mm) |
|---|---|---|---|---|---|---|---|---|
| 5.5 | 4 | 0 | 6.00 | 0.0851 | 20.25 | 0.661 | 0.002 | 7.59 |
| 5.8 | | 0 | 6.00 | | | | | |
| 5.8 | 5 | 3 | 6.00 | 0.084 | 18.5 | 1.46 | 0.0025 | 7.27 |
| 5.8 | 7 | 5 | 6.00 | 0.098 | 18.15 | 1.13 | 0.0025 | 7.01 |
| 5.8 | 6 | 5 | 6.00 | 0.093 | 18.15 | 1.13 | 0.0025 | 7.03 |
| 5.8 | 6 | 5 | 6.00 | 0.096 | 19.07 | 0.807 | 0.0025 | 7.33 |
| 5.8 | 6.5 | 5 | 6.00 | 0.053 | 17.72 | 0.982 | 0.0025 | 6.66 |
| 5.8 | 6 | 5 | 6.00 | 0.063 | 18.79 | 1.16 | 0.0025 | 7.16 |
| 5.8 | 7 | 7 | 6.00 | 0.08 | 18.25 | 1.28 | 0.0025 | 6.9 |
| 5.8 | 6 | 15 | 6.00 | 0.052 | 17.4 | 1.69 | 0.0025 | 6.51 |
| 5.8 | 8 | 25 | 6.00 | 0.0497 | 15.53 | 2.33 | 0.0025 | 6.23 |
| 5.8 | | 50 | 6.00 | | | | | |
| 5.8 | | 100 | 6.00 | | | | | |
| 5.8 | | 0 | 6.00 | | | | | |
| 5.8 | | 3 | 6.00 | | | | | |
| 5.8 | | 5 | 6.00 | | | | | |
| 5.8 | | 7 | 6.00 | | | | | |

TABLE 2-continued

| | | | | | | | | |
|---|---|---|---|---|---|---|---|---|
| 5.8 | 15 | 6.00 | | | | | | |
| 5.8 | 25 | 6.00 | | | | | | |
| 5.5 | 0 | 6.00 | 0.197 | 15.4 | 0.45 | 0.002 | 8.7 | |
| 5.5 | 5 | 6.00 | 0.24 | 13.1 | 0.74 | 0.002 | 8.3 | |
| 5.5 | 15 | 6.00 | 0.24 | 12 | 0.03 | 0.002 | 8.5 | |
| 5.5 | 25 | 6.00 | | | | | | |
| 5.5 | 40 | 6.00 | | | | | | |
| 5.5 | 50 | 6.00 | 0.173 | 10.3 | 0.5 | 0.002 | 7.42 | |
| 5.5 | 70 | 6.00 | | | | | | |
| 5.5 | 100 | 6.00 | 0.12 | 11.1 | 0.005 | 0.002 | 6.97 | |
| 6.2 | 0 | 6.00 | | | | | | |
| 6.2 | 3 | 6.00 | | | | | | |
| 6.2 | 5 | 6.00 | | | | | | |
| 6.2 | 8 | 6.00 | | | | | | |
| 6.2 | 0 | 6.00 | | | | | | |
| 6.2 | 3 | 6.00 | | | | | | |
| 6.2 | 5 | 6.00 | | | | | | |
| 6.2 | 8 | 6.00 | | | | | | |
| 6.2 | 0 | 6.00 | | | | | | |
| 6.2 | 3 | 6.00 | | | | | | |
| 6.2 | 5 | 6.00 | | | | | | |

TABLE 3

| Parison French size (O.D.) | Material Desc. | Vendor Mat'l. Lot # | Lot # | Mat'l. Formulation | Avg. Tensile (lb.) | Std. Dev | Elongation | Std. Dev |
|---|---|---|---|---|---|---|---|---|
| 6.2 | R&D1138 | S66758/S68042 | P137433 | 6333SNO1 + 7233SAO1 W/10% PA12w/3% XL | 25.933 | 3.108 | 9.646 | 0.9162 |
| 6.2 | R&D1138 | S66758/S68042 | P137433 | 6333SNO1 + 7233SAO1 W/10% PA12w/3% XL | 25.597 | 3.0236 | 9.189 | 1.239 |
| 6.2 | R&D1138 | S66758/S68042 | P137433 | 6333SNO1 + 7233SAO1 W/10% PA12w/3% XL | 25.884 | 1.554 | 10.01 | 0.616 |
| 6.9 | R&D1138 | S68541 | P138860 | 7233SAO1 W/10% PA12w/3% XL | 32.284 | 2.73 | 12.779 | 1.27 |
| 6.9 | R&D1138 | S68541 | P138860 | 7233SAO1 W/10% PA12w/3% XL | 28.813 | 2.874 | 7.325 | 0.833 |
| 6.9 | R&D1138 | S68541 | P138860 | 7233SAO1 W/10% PA12w/3% XL | 27.19 | 1.399 | 6.699 | 0.38 |
| 6.9 | R&D1138 | S68541 | P138860 | 7233SAO1 W/10% PA12w/3% XL | 28.04 | 1.707 | 6.813 | 0.441 |
| 6.9 | R&D1138 | S68541 | P138860 | 7233SAO1 W/10% PA12w/3% XL | 26.263 | 2.33 | 5.918 | 0.599 |
| 7.6 | R&D1138 | S68541 | P138885 | 7233SAO1 W/10% PA12w/3% XL | 33.75 | 3.593 | 11.861 | 1.253 |
| 7.6 | R&D1138 | S68541 | P138885 | 7233SAO1 W/10% PA12w/3% XL | 31.242 | 1.784 | 6.799 | 0.4 |
| 7.6 | R&D1138 | S68541 | P138885 | 7233SAO1 W/10% PA12w/3% XL | 30.434 | 2.437 | 6.1976 | 0.554 |
| 7.6 | R&D1138 | S68541 | P138885 | 7233SAO1 W/10% PA12w/3% XL | 28.015 | 0.95 | 6.141 | 0.24 |
| 7.6 | R&D1138 | S68541 | P138885 | 7233SAO1 W/10% PA12w/3% XL | 26.751 | 1.417 | 5.087 | 0.337 |
| 7.6 | R&D1138 | S68541 | P138885 | 7233SAO1 W/10% PA12w/3% XL | 25.216 | 1.366 | 4.385 | 0.408 |
| 8.5 | R&D1138 | S68541 | P138886 | 7233SAO1 W/10% PA12w/3% XL | 48.668 | 2.033 | 14.768 | 0.673 |
| 8.5 | R&D1138 | S68541 | P138886 | 7233SAO1 W/10% PA12w/3% XL | 36.825 | 2.034 | 6.604 | 0.346 |
| 8.5 | R&D1138 | S68541 | P138886 | 7233SAO1 W/10% PA12w/3% XL | 37.611 | 2.643 | 6.744 | 0.598 |
| 8.5 | R&D1138 | S68541 | P138886 | 7233SAO1 W/10% PA12w/3% XL | 33.328 | 1.486 | 6.209 | 0.536 |
| 8.5 | R&D1138 | S68541 | P138886 | 7233SAO1 W/10% PA12w/3% XL | 31.665 | 0.813 | 5.576 | 0.244 |
| 9.9 | R&D1138 | S68541 | P138887 | 7233SAO1 W/10% PA12w/3% XL | 67 | 5.628 | 16.82 | 1.259 |
| 9.9 | R&D1138 | S68541 | P138887 | 7233SAO1 W/10% PA12w/3% XL | 52.887 | 2.485 | 8.579 | 0.642 |
| 9.9 | R&D1138 | S68541 | P138887 | 7233SAO1 W/10% PA12w/3% XL | 59.914 | 1.943 | 9.888 | 0.665 |
| 9.9 | R&D1138 | S68541 | P138887 | 7233SAO1 W/10% PA12w/3% XL | 63.975 | 4.47 | 10.121 | 0.734 |
| 9.9 | R&D1138 | S68541 | P138887 | 7233SAO1 W/10% PA12w/3% XL | 58.594 | 1.964 | 8.338 | 0.278 |
| 9.9 | R&D1138 | S68541 | P138887 | 7233SAO1 W/10% PA12w/3% XL | 51.635 | 1.417 | 6.892 | 0.321 |

| Parison French size (O.D.) | Normal Pressure (atm) | Mrad | Nominal Balloon Diameter (mm) | Compliance (mm/atm) | Avg. Burst (atm) | Std. Dev (atm) | Double Wall (in) | Mean Burst Diameter (mm) |
|---|---|---|---|---|---|---|---|---|
| 6.2 | | 6 | 6.00 | | | | | |
| 6.2 | | 7 | 6.00 | | | | | |
| 6.2 | | 8 | 6.00 | | | | | |
| 6.9 | | 0 | 6.00 | | | | | |
| 6.9 | | 3 | 6.00 | | | | | |
| 6.9 | | 5 | 6.00 | | | | | |
| 6.9 | | 7 | 6.00 | | | | | |
| 6.9 | | 15 | 6.00 | | | | | |
| 7.6 | | 0 | 10.00 | | | | | |
| 7.6 | | 3 | 10.00 | | | | | |
| 7.6 | | 5 | 10.00 | | | | | |
| 7.6 | | 7 | 10.00 | | | | | |
| 7.6 | | 15 | 10.00 | | | | | |

TABLE 3-continued

| | | |
|---|---|---|
| 7.6 | 25 | 10.00 |
| 8.5 | 0 | 12.00 |
| 8.5 | 5 | 12.00 |
| 8.5 | 7 | 12.00 |
| 8.5 | 15 | 12.00 |
| 8.5 | 25 | 12.00 |
| 9.9 | 0 | 12.00 |
| 9.9 | 3 | 14.00 |
| 9.9 | 5 | 14.00 |
| 9.9 | 7 | 14.00 |
| 9.9 | 15 | 14.00 |
| 9.9 | 25 | 14.00 |

TABLE 4

| Parison French size (O.D.) | Material Desc. | Vendor Mat'l. Lot # | Lot # | Mat'l. Formulation | Mrad | Nominal Balloon Diameter (mm) | Compliance (mm/atm) | Avg. Burst (atm) | Std. Dev (atm) | RBP (atm) | Double Wall (in) | Mean Burst Diameter (mm) |
|---|---|---|---|---|---|---|---|---|---|---|---|---|
| 6.1 | R&D1202 | S70350 | P139685 | 7235SAO1 w/1/8% XL | 0 | 6.00 | 0.178 | 17.58 | 0.459 | 15.29 | 0.0025 | 8.75 |
| 6.1 | R&D1202 | S70350 | P139685 | 7235SAO1 w/1/8% XL | 0.5 | 6.00 | 0.194 | 17.08 | 0.22 | 15.93 | 0.0025 | 9.05 |
| 6.1 | R&D1202 | S70350 | P139685 | 7235SAO1 w/1/8% XL | 1 | 6.00 | 0.168 | 16.98 | 0.025 | 16.85 | 0.0025 | 8.77 |
| 6.1 | R&D1202 | S70350 | P139685 | 7235SAO1 w/1/8% XL | 2 | 6.00 | 0.157 | 16.37 | 0.483 | 13.86 | 0.0025 | 8.35 |
| 6.1 | R&D1202 | S70350 | P139685 | 7235SAO1 w/1/8% XL | 3 | 6.00 | 0.174 | 16.96 | 0.081 | 16.54 | 0.0025 | 8.84 |
| 6.1 | R&D1202 | S70350 | P139685 | 7235SAO1 w/1/8% XL | 5 | 6.00 | 0.17 | 15.13 | 0.303 | 14.55 | 0.0025 | 8.38 |
| 6.1 | R&D1202 | S70350 | P139685 | 7235SAO1 w/1/8% XL | 7 | 6.00 | 0.146 | 15.91 | 0.297 | 14.37 | 0.0025 | 7.94 |
| AVERAGES | | | | | | | 0.1739 | 16.73 | 0.267 | 15.34 | 0.0025 | 8.58 |
| 6.1 | R&D1203 | S70351 | P139587 | 7233SAO1 w/1/4% XL | 0 | 6.00 | 0.198 | 17.24 | 0.603 | 14.1 | 0.0025 | 9.00 |
| 6.1 | R&D1203 | S70351 | P139587 | 7233SAO1 w/1/4% XL | 0.5 | 6.00 | 0.188 | 17.84 | 0.324 | 16.15 | 0.0025 | 8.9 |
| 6.1 | R&D1203 | S70351 | P139587 | 7233SAO1 w/1/4% XL | 1 | 6.00 | 0.18 | 17.59 | 0.45 | 15.24 | 0.0025 | 8.6 |
| 6.1 | R&D1203 | S70351 | P139587 | 7233SAO1 w/1/4% XL | 2 | 6.00 | 0.129 | 16.96 | 0.054 | 16.88 | 0.0025 | 7.76 |
| 6.1 | R&D1203 | S70351 | P139587 | 7233SAO1 w/1/4% XL | 3 | 6.00 | 0.131 | 15.96 | 0.037 | 16.77 | 0.0025 | 7.88 |
| 6.1 | R&D1203 | S70351 | P139587 | 7233SAO1 w/1/4% XL | 5 | 6.00 | 0.127 | 16.77 | 0.373 | 14.82 | 0.0025 | 7.8 |
| 6.1 | R&D1203 | S70351 | P139587 | 7233SAO1 w/1/4% XL | 7 | 6.00 | 0.117 | 16.11 | 0.147 | 15.37 | 0.0025 | 7.53 |
| AVERAGES | | | | | | | 0.1529 | 17.07 | 0.284 | 5.58 | 0.0025 | 8.21 |
| 6.1 | R&D1137 | S70349 | P139588 | 7233SAO1 w/1/2% XL | 0 | 6.00 | 0.154 | 16.88 | 0.333 | 15.08 | 0.0025 | 8.20 |
| 6.1 | R&D1137 | S70349 | P139588 | 7233SAO1 w/1/2% XL | 0.5 | 6.00 | 0.15 | 18.19 | 0.417 | 16.02 | 0.0025 | 9.07 |
| 6.1 | R&D1137 | S70349 | P139588 | 7233SAO1 w/1/2% XL | 1 | 6.00 | 0.153 | 18.09 | 0.548 | 15.24 | 0.0025 | 8.2 |
| 6.1 | R&D1137 | S70349 | P139588 | 7233SAO1 w/1/2% XL | 2 | 6.00 | 0.14 | 17.55 | 0.463 | 15.15 | 0.0025 | 8.06 |
| 6.1 | R&D1137 | S70349 | P139588 | 7233SAO1 w/1/2% XL | 3 | 6.00 | 0.136 | 17 | 0.029 | 15.85 | 0.0025 | 8.06 |
| 6.1 | R&D1137 | S70349 | P139588 | 7233SAO1 w/1/2% XL | 5 | 6.00 | 0.108 | 16.75 | 0.465 | 14.33 | 0.0025 | 7.43 |
| 6.1 | R&D1137 | S70349 | P139588 | 7233SAO1 w/1/2% XL | 7 | 6.00 | 0.095 | 16.02 | 0.125 | 15.37 | 0.0025 | 7.16 |
| AVERAGES | | | | | | | 0.1337 | 17.21 | 0.34 | 5.44 | 0.0025 | 8.03 |
| 6.1 | R&D1102 | S70348 | 139689 | 7233SAO1 w/1% XL | 0 | 6.00 | 0.168 | 16.98 | 0.465 | 14.56 | 0.0025 | 7.52 |
| 6.1 | R&D1102 | S70348 | 139689 | 7233SAO1 w/1% XL | 0.5 | 6.00 | 0.107 | 18.12 | 0.308 | 16.51 | 0.0025 | 7.44 |
| 6.1 | R&D1102 | S70348 | 139689 | 7233SAO1 w/1% XL | 1 | 6.00 | 0.113 | 18.04 | 0.448 | 15.71 | 0.0025 | 7.42 |
| 6.1 | R&D1102 | S70348 | 139689 | 7233SAO1 w/1% XL | 2 | 6.00 | 0.108 | 17.95 | 0.305 | 16.36 | 0.0025 | 7.37 |
| 6.1 | R&D1102 | S70348 | 139689 | 7233SAO1 w/1% XL | 3 | 6.00 | 0.11 | 17.94 | 0.298 | 16.38 | 0.0025 | 7.36 |
| 6.1 | R&D1102 | S70348 | 139689 | 7233SAO1 w/1% XL | 5 | 6.00 | 0.096 | 17.54 | 0.479 | 15.15 | 0.0025 | 7.03 |
| 6.1 | R&D1102 | S70348 | 139689 | 7233SAO1 w/1% XL | 7 | 6.00 | 0.081 | 17.11 | 0.602 | 13.98 | 0.0025 | 6.90 |
| AVERAGES | | | | | | | 0.112 | 17.08 | 0.415 | 5.52 | 0.0025 | 7.31 |

What is claimed is:

1. A process for assembling a medical device, the medical device comprising an expandable balloon, and the process comprising:

creating a mixture of a polyamide elastomer and at least one additional cross-linking reactant, the cross-linking reactant comprising an aromatic molecule selected from the class consisting of 1,3,5 triethyl benzene; 1,2,4 triethyl benzene; and 1,3,5 triisopropyl benzene;

cross-linking the mixture of the polyamide elastomer and the at least one additional reactant by exposing the mixture to a suitable fluence of radiation; and forming the cross-linked mixture into the balloon.

2. The process according to claim 1,
wherein the step of cross-linking the mixture of the polyamide elastomer and the at least one additional reactant involves cross-linking the at least one additional reactant with the polyamide elastomer.

3. The process according to claim 1, wherein the process is carried out with about 0.5 to about 1.5 percent by weight of the aromatic molecule.

4. The process according to claim 1, wherein the process is carried out with an amount of the at least one cross-linking reactant sufficient to give the balloon a strength about equal to that of a balloon composed of a nylon block copolymer and comparably cross-linked by irradiation, but in the absence of any cross-linking reactant, agent or promoter.

5. The process according to claim 1, wherein cross-linking of the mixture of the polyamide elastomer and the at least one additional reactant comprises irradiating the mixture with an electron beam or with ultraviolet, X-rays or gamma rays.

6. The process according to claim 1, wherein the cross-linking of the mixture of the polyamide elastomer and the at least one additional reactant is carried out at a total fluence of about 0.5 to about 20 megarads.

7. The process according to claim 1, wherein the mixing of the polyamide elastomer and the at least one additional reactant is carried out by compounding.

8. The process according to claim 1, further comprising forming the mixture of the polyamide elastomer and the at least one additional reactant into tubing, from which the balloon is formed.

9. The process according to claim 8, wherein the tubing is formed by extruding the mixture of the polyamide elastomer and the at least one additional reactant.

10. The process according to claim 8, wherein the mixture of the polyamide elastomer and the at least one additional reactant is formed into the balloon by inflation of the tubing.

11. The process according to claim 1, wherein the medical device further comprises a catheter shaft, and wherein the process further comprises connecting the balloon to the catheter shaft.

12. The process according to claim 11, wherein connecting the balloon to the catheter shaft is carried out by adhesion.

13. The process according to claim 11, wherein connecting the balloon to the catheter shaft is carried out by thermal bonding.

14. The process according to claim 1, wherein the process is carried out with at least one polyamide elastomer selected from the class consisting of polyester amides, polyether ester amides and polyether amides.

15. The process according to claim 14, wherein the process is carried out with a polyamide elastomer comprising a nylon block copolymer.

16. The process according to claim 15, wherein the process is carried out with a nylon block copolymer including polyether blocks separated by polyamide blocks.

* * * * *

UNITED STATES PATENT AND TRADEMARK OFFICE
CERTIFICATE OF CORRECTION

PATENT NO.        : 7,485,250 B2
APPLICATION NO.   : 10/463749
DATED             : February 3, 2009
INVENTOR(S)       : Scott E. Boatman et al.

It is certified that error appears in the above-identified patent and that said Letters Patent is hereby corrected as shown below:

Column 24, claim 3, lines 50-51, delete "about 0.5 to about 1.5 percent by weight of the aromatic molecule." and substitute --a mixture comprising about 1 to about 2 percent by weight of the difunctional material; about 0.5 to about 1.5 percent by weight of the trifunctional material or the aromatic molecule; or about 0.01 to about 1 percent by weight of the tetrafunctional material.-- in its place.

Signed and Sealed this

Twenty-first Day of July, 2009

JOHN DOLL
*Acting Director of the United States Patent and Trademark Office*